US011344561B2

(12) United States Patent
Walker

(10) Patent No.: US 11,344,561 B2
(45) Date of Patent: May 31, 2022

(54) TREATMENT OF SUBMENTAL FAT

(71) Applicant: Allergan Sales, LLC, Madison, NJ (US)

(72) Inventor: Patricia Walker, Parsippany, NJ (US)

(73) Assignee: Allergan Sales, LLC, Madison, NJ (US)

(*) Notice: Subject to any disclaimer, the term of this patent is extended or adjusted under 35 U.S.C. 154(b) by 0 days.

(21) Appl. No.: 15/498,575

(22) Filed: Apr. 27, 2017

(65) Prior Publication Data
US 2017/0290848 A1 Oct. 12, 2017

Related U.S. Application Data

(63) Continuation of application No. 13/399,960, filed on Feb. 17, 2012, now abandoned.

(60) Provisional application No. 61/444,613, filed on Feb. 18, 2011.

(51) Int. Cl.
| A61K 31/575 | (2006.01) |
| A61K 31/56 | (2006.01) |
| A61K 9/00 | (2006.01) |
| A61K 31/167 | (2006.01) |
| A61K 38/46 | (2006.01) |
| A61K 45/06 | (2006.01) |
| A61K 47/10 | (2017.01) |
| A61K 47/24 | (2006.01) |

(52) U.S. Cl.
CPC .......... *A61K 31/575* (2013.01); *A61K 9/0019* (2013.01); *A61K 31/167* (2013.01); *A61K 31/56* (2013.01); *A61K 38/465* (2013.01); *A61K 45/06* (2013.01); *A61K 47/10* (2013.01); *A61K 47/24* (2013.01)

(58) Field of Classification Search
CPC .. A61K 9/0019; A61K 31/575; A61K 31/167; A61K 38/465; A61K 47/24; A61P 43/00; A61P 41/00
See application file for complete search history.

(56) References Cited

U.S. PATENT DOCUMENTS

| | | |
|---|---|---|
| 4,113,882 A | 9/1978 | Okazaki et al. |
| 4,117,121 A | 9/1978 | Gallo-Torres et al. |
| 4,158,707 A | 6/1979 | Steffen et al. |
| 4,664,910 A | 5/1987 | Caserio et al. |
| 4,681,876 A | 7/1987 | Marples et al. |
| 4,722,888 A | 2/1988 | Broder et al. |
| 4,851,435 A | 7/1989 | Sauer et al. |
| 4,866,044 A | 9/1989 | Sato et al. |
| 4,994,439 A | 2/1991 | Longenecker et al. |
| 5,085,864 A | 2/1992 | Cannon et al. |
| 5,288,498 A | 2/1994 | Stanley et al. |
| 5,326,562 A | 7/1994 | Scott |
| 5,344,822 A | 9/1994 | Levine et al. |
| 5,371,104 A | 12/1994 | Feigenbaum |
| 5,376,646 A | 12/1994 | Pittrof et al. |
| 5,395,545 A | 3/1995 | Fischer et al. |
| 5,506,218 A | 4/1996 | Parker et al. |
| 5,603,932 A | 2/1997 | Blaas et al. |
| 5,616,342 A | 4/1997 | Lyons |
| 5,674,855 A | 10/1997 | Levine et al. |
| 5,747,066 A | 5/1998 | Pittrof et al. |
| 5,759,445 A | 6/1998 | Yamamoto et al. |
| 5,849,883 A | 12/1998 | Boone et al. |
| 5,863,554 A | 1/1999 | Illum |
| 5,876,721 A | 3/1999 | Alexander et al. |
| 5,891,083 A * | 4/1999 | Capella ............ A61K 38/1709 435/267 |
| 5,914,390 A | 6/1999 | Nathan et al. |
| 5,942,248 A | 8/1999 | Barnwell |
| 5,952,313 A | 9/1999 | Carlson |
| 5,952,392 A | 9/1999 | Katz et al. |
| 6,024,961 A | 2/2000 | Curtiss et al. |
| 6,025,396 A | 2/2000 | Kim et al. |
| 6,120,805 A | 9/2000 | Spenlehauer et al. |
| 6,136,851 A | 10/2000 | Bonte et al. |
| 6,197,327 B1 | 3/2001 | Harrison et al. |
| 6,221,378 B1 | 4/2001 | Modi |
| 6,225,343 B1 | 5/2001 | Behl et al. |
| 6,251,428 B1 | 6/2001 | Yoo |
| 6,255,502 B1 | 7/2001 | Penkler et al. |
| 6,294,192 B1 | 9/2001 | Patel et al. |
| 6,313,128 B1 | 11/2001 | Blanc-Ferras et al. |
| 6,315,984 B1 | 11/2001 | Modi |

(Continued)

FOREIGN PATENT DOCUMENTS

| CA | 2033725 C | 5/2001 |
| CA | 2551474 A1 | 7/2005 |

(Continued)

OTHER PUBLICATIONS

Duncan D. Injection lipolysis for body contouring. Springer Berlin Heidelberg. 2010;59-70.*
Fit. The first UK injection technique recommendations. Becton, Dickinson and Company. 2010;1-13.*
Rotunda et al. Randomized double-blind clinical trial of subcutaneously injected deoxycholate versus a phosphatidylcholine-deoxycholate combination for the reduction of submental fat. Dermatol Surg. 2009;35(5):792-803.*
Hasengschwandtner F. Phosphatidylcholine treatment to induce lipolysis. Journal of Cosmetic Dermatology. 2005;4:308-313.*
U.S. Appl. No. 11/710,601, filed Feb. 23, 2007, Burkhart et al.
U.S. Appl. No. 12/397,229, filed Mar. 3, 2009, Hodge et al.

(Continued)

*Primary Examiner* — Lynn Y Fan
(74) *Attorney, Agent, or Firm* — Foley & Lardner LLP

(57) ABSTRACT

This disclosure relates to compositions, kits and methods for non-surgical reduction of localized subcutaneous fat such as that associated with a cosmetic fat accumulation. The methods employ compositions having specific concentrations of a salt of deoxycholic acid which provides a superior fat cell necrosis with modest adverse effects. Examples of localized subcutaneous fat are found in the submental area, in particular under the chin.

10 Claims, 14 Drawing Sheets

(56) References Cited

U.S. PATENT DOCUMENTS

| | | |
|---|---|---|
| 6,342,489 B1 | 1/2002 | Palmieri et al. |
| 6,350,458 B1 | 2/2002 | Modi |
| 6,375,975 B1 | 4/2002 | Modi |
| 6,383,471 B1 | 5/2002 | Chen et al. |
| 6,416,779 B1 | 7/2002 | D'Augustine et al. |
| 6,417,179 B1 | 7/2002 | Burkhart et al. |
| 6,451,286 B1 | 9/2002 | Modi |
| 6,489,312 B1 | 12/2002 | Stogniew et al. |
| 6,537,561 B1 | 3/2003 | Fukui et al. |
| 6,544,972 B1 | 4/2003 | Steer et al. |
| 6,573,299 B1 | 6/2003 | Petrus |
| 6,663,885 B1 | 12/2003 | Hager et al. |
| 6,713,470 B2 | 3/2004 | Jackson |
| 6,828,155 B1 | 12/2004 | Kaneko et al. |
| 6,849,263 B2 | 2/2005 | Modi |
| 6,884,768 B2 | 4/2005 | Kimura et al. |
| 7,052,716 B1 | 5/2006 | Lanzendorfer et al. |
| 7,166,299 B2 | 1/2007 | Yoo |
| 7,226,775 B2 | 6/2007 | Mapleson et al. |
| 7,303,768 B2 | 12/2007 | Yoo |
| 7,538,093 B2 | 5/2009 | Engler et al. |
| 7,622,130 B2 | 11/2009 | Kolodney et al. |
| 7,754,230 B2 | 7/2010 | Kolodney et al. |
| 8,101,593 B2 | 1/2012 | Hodge et al. |
| 8,258,146 B2 | 9/2012 | Morita et al. |
| 8,298,556 B2 | 10/2012 | Kolodney et al. |
| 8,367,649 B2 | 2/2013 | Hodge et al. |
| 8,367,852 B2 | 2/2013 | Prasad et al. |
| 8,461,140 B2 | 6/2013 | Moriarty et al. |
| 8,546,367 B2 | 10/2013 | Moriarty et al. |
| 8,609,707 B2 | 12/2013 | Palepu et al. |
| 8,653,058 B2 | 2/2014 | Hodge et al. |
| 8,791,270 B2 | 7/2014 | Brittain et al. |
| 8,846,066 B2 | 9/2014 | Kolodney et al. |
| 8,883,770 B2 | 11/2014 | Moriarty et al. |
| 9,050,349 B2 | 6/2015 | Moriarty et al. |
| 9,186,364 B2 | 11/2015 | Hodge et al. |
| 9,522,155 B2 | 12/2016 | Moriarty et al. |
| 9,636,349 B2 | 5/2017 | Moriarty et al. |
| 9,683,008 B2 | 6/2017 | Moriarty et al. |
| 9,724,356 B2 | 8/2017 | Hodge et al. |
| 9,737,549 B2 | 8/2017 | Hodge et al. |
| 9,987,291 B2 | 6/2018 | Moriarty et al. |
| 10,058,561 B2 | 8/2018 | Kolodney et al. |
| 10,071,105 B2 | 9/2018 | Hodge et al. |
| 10,500,214 B2 | 12/2019 | Hodge et al. |
| 10,946,030 B2 | 3/2021 | Hodge et al. |
| 2001/0051595 A1 | 12/2001 | Lyons et al. |
| 2002/0028766 A1 | 3/2002 | Papadimitriou |
| 2002/0031558 A1 | 3/2002 | Yoo |
| 2002/0032159 A1 | 3/2002 | Maruyama et al. |
| 2002/0058010 A1 | 5/2002 | Picard-Lesboueyries et al. |
| 2002/0107291 A1 | 8/2002 | De Tommaso |
| 2002/0168402 A1 | 11/2002 | Kipp et al. |
| 2003/0027833 A1 | 2/2003 | Cleary et al. |
| 2003/0035831 A1 | 2/2003 | Modi |
| 2003/0054981 A1 | 3/2003 | Milton et al. |
| 2003/0064097 A1 | 4/2003 | Patel et al. |
| 2003/0072807 A1 | 4/2003 | Wong et al. |
| 2003/0077329 A1 | 4/2003 | Kipp et al. |
| 2003/0161886 A1 | 8/2003 | Dickinson et al. |
| 2003/0186933 A1 | 10/2003 | Yoo |
| 2003/0219472 A1 | 11/2003 | Pauletti et al. |
| 2004/0022862 A1 | 2/2004 | Kipp et al. |
| 2004/0038952 A1 | 2/2004 | Feher |
| 2004/0067919 A1 | 4/2004 | Jee |
| 2004/0096494 A1 | 5/2004 | Siekmann et al. |
| 2004/0101569 A1 | 5/2004 | Rang |
| 2004/0115255 A1 | 6/2004 | Leigh et al. |
| 2004/0118412 A1 | 6/2004 | Piletti-Reyes |
| 2004/0141949 A1 | 7/2004 | Rosenthal et al. |
| 2004/0161407 A1 | 8/2004 | Kimura et al. |
| 2004/0201117 A1 | 10/2004 | Anderson |
| 2004/0213855 A1 | 10/2004 | Pettersson et al. |
| 2004/0220283 A1 | 11/2004 | Zhang et al. |
| 2005/0019404 A1 | 1/2005 | Sung et al. |
| 2005/0048126 A1 | 3/2005 | Rabinow et al. |
| 2005/0079228 A1 | 4/2005 | Jaiswal et al. |
| 2005/0089555 A1 | 4/2005 | Boderke et al. |
| 2005/0123582 A1 | 6/2005 | Sung et al. |
| 2005/0143347 A1 | 6/2005 | Boderke et al. |
| 2005/0158408 A1 | 7/2005 | Yoo |
| 2005/0163821 A1 | 7/2005 | Sung et al. |
| 2005/0261258 A1 | 11/2005 | Kolodney et al. |
| 2005/0266065 A1 | 12/2005 | Perrier et al. |
| 2005/0267080 A1 | 12/2005 | Kolodney et al. |
| 2005/0287199 A1 | 12/2005 | Denney et al. |
| 2006/0074057 A1 | 4/2006 | Marchewitz |
| 2006/0127468 A1* | 6/2006 | Kolodney ............... A61K 8/63 424/450 |
| 2006/0154906 A1 | 7/2006 | Kolodney et al. |
| 2006/0222673 A1 | 10/2006 | Chern et al. |
| 2006/0222695 A1 | 10/2006 | Zadini et al. |
| 2008/0058300 A1 | 3/2008 | McLane |
| 2008/0318870 A1 | 12/2008 | Moriarty et al. |
| 2009/0270642 A1 | 10/2009 | Prasad et al. |
| 2009/0275545 A1 | 11/2009 | Boderke et al. |
| 2010/0048527 A1 | 2/2010 | Kolodney et al. |
| 2010/0292650 A1 | 11/2010 | Kolodney et al. |
| 2011/0002896 A1 | 1/2011 | Kolodney et al. |
| 2011/0218181 A1 | 9/2011 | Hodge et al. |
| 2012/0083481 A1 | 4/2012 | Hodge et al. |
| 2012/0237492 A1 | 9/2012 | Walker |
| 2012/0258943 A1 | 10/2012 | Hodge et al. |
| 2013/0109282 A1 | 5/2013 | Lewkoski et al. |
| 2013/0190282 A1 | 7/2013 | Hodge et al. |
| 2014/0004206 A1 | 1/2014 | Kolodney et al. |
| 2014/0148429 A1 | 5/2014 | Hodge et al. |
| 2014/0155364 A1 | 6/2014 | Hodge et al. |
| 2015/0051182 A1 | 2/2015 | Kolodney et al. |
| 2017/0119794 A1 | 5/2017 | Beddingfield et al. |
| 2017/0136040 A1 | 5/2017 | Moriarty et al. |
| 2017/0319601 A1 | 7/2017 | Walker |
| 2017/0290848 A1 | 10/2017 | Walker |
| 2017/0342101 A1 | 11/2017 | Moriarty et al. |
| 2018/0000835 A1 | 1/2018 | Hodge et al. |
| 2018/0015105 A1 | 1/2018 | Hodge et al. |
| 2018/0338987 A1 | 11/2018 | Moriarty et al. |
| 2019/0015427 A1 | 1/2019 | Kolodney et al. |
| 2019/0038638 A1 | 2/2019 | Hodge et al. |
| 2020/0188414 A1 | 6/2020 | Hodge et al. |

FOREIGN PATENT DOCUMENTS

| | | |
|---|---|---|
| CN | 1348360 A | 5/2002 |
| EP | 0 208 519 A2 | 1/1987 |
| EP | 0 408 174 A1 | 1/1991 |
| EP | 0 426 029 A1 | 5/1991 |
| EP | 0 439 042 B1 | 6/1995 |
| EP | 0 439 513 B1 | 3/1996 |
| EP | 1 111 390 | 6/2001 |
| EP | 0 730 860 B1 | 1/2002 |
| EP | 0 806 940 B1 | 4/2003 |
| EP | 1 005 324 B1 | 3/2005 |
| EP | 2 561 876 A1 | 2/2013 |
| JP | 61-158995 | 7/1986 |
| JP | 03-048622 | 3/1991 |
| JP | 04-235918 | 8/1992 |
| JP | 11-240835 | 9/1999 |
| JP | 2007-515439 | 6/2007 |
| JP | 2007-515494 | 6/2007 |
| JP | 2007-538104 | 12/2007 |
| JP | 2008-530005 A | 8/2008 |
| JP | 2010-222283 | 10/2010 |
| KR | 10-2007-0110351 | 11/2007 |
| WO | WO-90/12583 A1 | 11/1990 |
| WO | WO-93/05811 A1 | 4/1993 |
| WO | WO-94/04177 A1 | 3/1994 |
| WO | WO-1996/006635 A1 | 3/1996 |
| WO | WO-99/15152 A1 | 4/1999 |
| WO | WO-00/04875 A1 | 2/2000 |
| WO | WO-00/13029 | 3/2000 |
| WO | WO-01/70151 A1 | 9/2001 |
| WO | WO-02/058610 A1 | 8/2002 |

(56) References Cited

FOREIGN PATENT DOCUMENTS

| | | |
|---|---|---|
| WO | WO-03/018134 A2 | 3/2003 |
| WO | WO-03/082340 A1 | 10/2003 |
| WO | WO-03/094894 A1 | 11/2003 |
| WO | WO-2004/010941 A2 | 2/2004 |
| WO | WO-2004/039326 A2 | 5/2004 |
| WO | WO-2005/020894 A2 | 3/2005 |
| WO | WO-2005/061004 A1 | 7/2005 |
| WO | WO-2005/063169 A2 | 7/2005 |
| WO | WO-2005/063205 | 7/2005 |
| WO | WO-2005/112942 A1 | 12/2005 |
| WO | WO-2005/117832 A1 | 12/2005 |
| WO | WO-2005/117900 A1 | 12/2005 |
| WO | WO-2006/007675 A1 | 1/2006 |
| WO | WO-2006/086038 A1 | 8/2006 |
| WO | WO-2006/133160 A2 | 12/2006 |
| WO | WO-2009/131995 A1 | 10/2009 |
| WO | WO-2009/132342 A1 | 10/2009 |
| WO | WO-2011/075701 A2 | 6/2011 |
| WO | WO-2012/112940 A1 | 8/2012 |

OTHER PUBLICATIONS

U.S. Appl. No. 13/753,366, filed Jan. 29, 2013, Hodge et al.
"Health Alert: Lipostabil" http://kyw.com/health/local_storL336152706.html, Dec. 2, 2002.
"Lose those love handles" A CBS HealthWatch Special Report http://cbsnewyork.com/healthwatch/local story 329141707.html, Nov. 25, 2002.
"Love handles can be shrunk without surgery" http://www.macleans.ca/topstories/health/article.jsp?content=20040225_090843_4800, Feb. 25, 2004.
"Deoxycholic acid", Product Information, SIGMA, 2002.
Ablon, et al., "Treatment of lower eyelid fat pads using phosphatidylcholine: clinical trial and review," Derm. Surgery, (2004), 30(3):422-427.
Alkan-Onyuksel H, Ramakrishnan S, Chai HB, Pezzuto JM. A mixed micellar formulation suitable for the parenteral administration of taxol. Pharm Res 1994, 11:206-12.
Almgren M. Mixed micelles and other structures in the solubilization of bilayer lipid membranes by surfactants. Biochim Biophys Acta 2000,1508:146-63.
Asaadi M, Salas AP, Motamedi B. Mesoplasty: a new approach to non-surgicalliposculpture. Plastic Surgery 2004, Oct. 10, 2004, Philadelphia, PA.
ASAPS. American Society for Aesthetic Plastic Surgery. Lipoplasty (liposuction) without surgery?, Oct. 2002.
Banerjee P, Joo JB, Buse JT, Dawson G. Differential solubilization of lipids along with membrane proteins by different classes of detergents. Chem Phys Lipids 1995, 77:65-78.
Bates B. 'Fat dissolving' substance injects CCs of controversy. Skin and Allergy News 2003,34.
Baumann LS. Phosphatidylcholine. Skin and Allergy News 2003, 34.
Bayer_ Press Release, "First Patients enrolled in EU Phase III Clinical Development Program to evaluate ATX-101 for reduction of Submental Fat," (2008).
Bellman B. Phosphatidylcholine reaction. Skin and Allergy News 2003, 34.
Bryant, R., Controversial mesotherapy: could it be the next botox. Dermatology Times, Dec. 2004, 1-2.
Buko V, Lukivskaya O, Nikitin V, Tarasov Y, Zavodnick L, Borodinsky A, Gorenshtein B, Janz B, Gundermann K-J, Schumacher R. Hepatic and pancreatic effects of polyenoylphosphatidylcholine in rats with alloxan-induced diabetes. Cell Biochem Function 14:131-7, 1996.
Canty D, Zeisel S, Jolitz A. Lecithin and choline: research update on health and nutrition. Fort Wayne, IN: Central Soya Company, Inc., 1998.
Chalmers K. Fat loss a needle away. http://surgerynews.net/news/0204/meso020402.htm, Feb. 1, 2004.

Davidson et al. "Limitations of phosphatidylcholine/deoxycholate mixtures for the analysis of phospholipase A2 inhibition and activation: illustration with annexins." Biochimica et Biophysica Acta, 1992, 1127(3):270-276.
Duncan et al., "Fat Reduction Using Phosphatidylcholine/Sodium Deoxycholate Injections: Standard of Practice", Aesthetic Plastic Surgery, 2008, 32(6):858-872.
Duncan et al., "Lipodissolve for Subcutaneous Fat Reduction and Skin Retraction," Aesthetic Surgery Journal, (2005), 25(5):530-543.
Duncan et al.: "Injectable therapies for localized fat loss: state of the art.", Clinics in Plastic Surgery, 2011, LNKDPUBMED:21824545, vol. 38, No. 3, 2011, pp. 489-501.
Durr M, Hager J, Lohr JP. Investigation on mixed micelle and liposome preparations for parental use on soya phosphatidylcholine. Eur J Pharm Biopharm 1994, 40: 147-56.
Ebihara L, Hall JE, MacDonald RC, Mcintosh TJ, Simon SA. Effect of benzyl alcohol on lipid bilayers. A comparisons of bilayer systems. Biophys J 1979,28:185-96.
Engelke M, Jessel R, Wiechmann A, Diehl HA. Effect of inhalation anaesthetics on the phase behaviour, permeability and order of phosphatidylcholine bilayers. Biophys Chem 1997,67:127-38.
FDA news release: "FDA issues warning letters for drugs promoted in fat elimination procedure", 2010, Retrieved from the Internet: URL:http://www.fda.gov/NewsEvents/Newsroom/PressAnnouncements/ucm207453.htm [retrieved on Oct. 18, 2011].
Goldman L, Bennet JC, Cecil RL. Cecil Textbook of Medicine. St. Louis, MO: W.B. Saunders Co., 2001.
Gordon LM, Sauerheber RD, Esgate JA, Dippie I, Marchmont RJ, Houslay MD. The increase in bilayer fluidity of rat liver plasma membranes achieved by the local anesthetic benzyl alcohol affects the activity of intrinsic membrane enzymes. J Biol Chem 1980, 255:4519-27.
Gustafson C, Tagesson C. Influence of organic solvent mixtures on biological membranes. Br J Ind Med 1985, 42:591-5.
Hammad MA, Muller BW. Increasing drug solubility by means of bile salt-phosphatidylcholine-based mixed micelles. Eur J Pharm Biopharm 1998, 46:361-7.
Heerklotz H, Seelig J. Correlation of membrane/water partition coefficients of detergents with the critical micelle concentration. Biophys J 2000, 78:2435-40.
Hexsel, et al., "Phosphatidylcholine in the treatment of localized fat," J. Drugs Dermatol., (2003), 2(5):511-518.
Hofmann et al., "Bile acid solubility and precipitation in vitro and in vivo: the role of conjugation, pH, and Ca2+ ions", Journal of Lipid Research, vol. 33, pp. 617-626 (1992).
Hutchison, ABC News Medical Unit: "Docs Question Bayer's Injection for Dissolving Double Chin", 2011, Retrieved from Internet: URL:http://abcnews.go.com/Health/WellnessNews/bayer-tests-fat-loss-injection-double-chin/story?id=12600333, [retrieved on May 22, 2014].
Igimi et al., "pH-Solubility relations of chenodeoxycholic and ursodeoxycholic acids: physical-chemical basis for dissimilar solution and membrane phenomena", Journal of Lipid Research, vol. 21, pp. 72-90 (1980).
International Search Report and Written Opinion dated Jun. 1, 2012 in related PCT Application No. PCT/US2011/048806.
International Search Report and Written Opinion dated Nov. 7, 2011 in related PCT Application No. PCT/US2011/031284.
Jones MN. Surfactants in membrane solubilisation. Int J Pharm 1999, 177:137-59.
Kawanaka et al., NASH, Japanese Journal of Liver, Biliary tract, and Pancreas, 2002, 44(4):521-526.
Kern, et al., "Regulation of Lipoprotein Lipase Immunoreactive Mass in Isolated Human Adipocytes", J. Clin. Invest., vol. 81, pp. 398-406; (1988).
Klein, et al., "A New Method to Quantify the Effect After Subcutaneous Injection of Lipolytic Substances," Aesth Plast Surg., (2008), 32:667-672.
Kolonin, et al., "Reversal of obesity by targeted ablation of adipose tissue," Nature Medicine, Nature Publishing Group, (2004) 10(6): 625-632.

(56) References Cited

OTHER PUBLICATIONS

Kythera Biopharmaceuticals: "Evaluation of safety and efficacy of ATX-101 in the reduction of submental fat", 2011, Retrieved from the Internet: URL:http://clinicaltrials.gov/ct2/show/NCT01294644, [retrieved on Feb. 28, 2011].
Kythera Biopharmaceuticals: "Evaluation of Safety and Efficacy of ATX-101 in the Reduction of Submental Fat", 2011, Retrieved from the Internet: URL:http://clinicaltrials.gov/ct2/show/NCT01305577 [retrieved on Jan. 2, 2015].
Kythera Newsroom. Two Phase 2 studies with ATX-101—study results demonstrated statistically significant reduction in patients' unwanted submental fat. Kythera Biopharmaceuticals, Inc. (2009), 1-2.
Landman B. Beyond Botox. http://newyorkmetro.com/nymetro/health/bestdoctors/cosmeticsurgery/2003/n-.sub.--9281/index.html.
Learn about lecithins. Oxford, CT: American Lecithin Company, 2003.
Lester DS, Baumann D. Action of organic solvents on protein kinase C. Eur J Pharmacol 1991, 206:301-8.
Lichtenberg D, Robson RJ, Dennis EA. Solubilization of phospholipids by detergents. Structural and kinetic aspects. Biochim Biophys Acta 1983, 737:285-304.
Lichtenberg D, Zilberman Y, Greenzaid P, Zamir S. Structural and kinetic studies on the solubilization of lecithin by sodium deoxycholate. Biochemistry 1979, 18:3517-25.
Lichtenberg D. Characterization of the solubilization of lipid bilayers by surfactants. Biochim Biophys Acta 1985, 821:470-8.
Lieber CS, Robins SJ, Li J, DeCarli LM, Mak KM, Fasulo JM, Leo MA. Phosphatidylcholine protects againstfibrosis and cirrhosis in the baboon. Gastroenterology 106: 152-9, 1994.
Lipostabil. Rhone-Poulenc Rorer. Cologne, West Germany: Natterman International GMBH, 1990.
McCaslin, "Detergent Properties", Encyclopedia of Biological Chemistry, vol. 1, pp. 577-581 (2004).
Milovic et al. Effects of deoxycholate on human colon cancer cells: apoptosis or proliferation. European Journal of Clinical Investigation. (2002) 32(1):29-34.
Moy, LS. Phosphatidylcholine injections: a study measuring decreased subcutaneous fat thickness. Combined Annual Meeting of the American Society for Dermatologic Surgery and the American Society of Mohs Micrographic Surgery and Cutaneous Oncology, San Diego, CA Sep. 30-Oct. 3, 2004.
Parnham MJ, Wendel A. Phospholipids and liposomes—safety for cosmetical and pharmaceutical use. Nattermann Phospholipid GMBH Scientific Publication No. 2 1995.
Powell, A. A. et al. Bile acid hydrophobicity is correlated with induction of apoptosis and/or growth arrest in HCT116 cells. Biochem. J. 2001; 356:481-486.
Rittes PG. "The Use of Phosphatidylcholine for Correction of Lower Lid Bulging Due to Prominent Fat Pads," Dermatologic Surgery, (2001, vol. 27:4, 391-392.
Rittes, P. G., "The use of phosphatidylcholine for correction of localized fat deposits," Aesthetic Plast. Surg., (2003), 27(4):315-318.
Rosenbaum, M., An exploratory investigation of the morphology and biochemistry of cellulite, Annual Meeting of American Society for Aesthetic Surgery, New York, May 1997, 1934-39.
Rossi ABR, Vergnanini AL. Cellulite: a review. JEADV 14:251-62, 2000.
Rotunda A, Suzuki H, Moy RL, Kolodney MS. Detergent effects of sodium deoxycholate are a major feature of injectable phosphatidylcholine. American Society for Dermatologic Surgery, New Orleans, LA, Oct. 11, 2003.
Rotunda et al. "Lipomas treated with subcutaneous deoxycholate injections". J. Am. Acad. Dermatol., (2005) pp. 973-978.
Rotunda et al. "Mesotherapy and Phosphatidylcholine Injections: Historical Clarification and Review" Dermatologic Surgery, (2006) 32: 465-480.
Rotunda et al., "Randomized double-blind clinical trial of subcutaneously injected deoxycholate versus a phosphatidylcholine-deoxycholate combination for the reduction of submental fat", Dermatologic Surgery, 2009, 35(5):792-803.
Rotunda, et al. "Detergent Effects of Sodium Deoxycholate Are a Major Feature of an Injectable Phosphatidylcholine Formulation Used for Localized Fat Dissolution" Dermatologic Surgery, 2004, vol. 30, pp. 1001-1008.
Sager S. New fat removal technique getting raves: Is it safe? Does it work? http://abclocal.go.com/wabc/news/wabc.sub.--020703.sub.--mesotherap-y.html, Feb. 7, 2003.
Salti, et al., "Phosphatidylcholine and Sodium Deoxycholate in the Treatment of Localized Fat: A Double-Blind, Randomized Study," Dermatol Surg., (2008), 34:60-66.
Schuck S, Honsho M, Ekroos K, Shevchenko A, Simons K. Resistance of cell membranes to different detergents. Proc Natl Acad Sci 2003, 100:5795-800.
Sergio, M. Traitement mesotherapique des xanthelasmas a la phophatidilcoline polyinsaturee (EPL). V Congres Internacional de Mesotherapie, Paris: Dermatologie, 1988; 364.
Serra M., Subcutaneous infiltration with phosphatidylcholine solution for treatment of buffalo hump and fatty pads. 3rd Int'l workshop on adverse drug reactions and lipodystrophy in HIV, Athens, Oct. 2001, 115.
Shimazawa et al., "Involvement of ER stress in retinal cell death", Mol Vis, 2007, 13:578-587.
Sigma: "RIPA Buffer", 2003, retrieved from the internet: URL:http://www.sigmaaldrich.com/etc/medialib/docs/Sigma/Bulletin/r0278bul.Par.0001.File.tmp/r0278bul.pdf.
Singer SJ, Nicolson GL. The fluid mosaic model of the structure of cell membranes. Science 1972, 175:720-31.
Small, "Size and Structure of Bile Salt Micelles. Influence of Structure, Concentration, Counterion Concentration, pH, and Temperature", In Molecular Association in Biological and Related Systems; Goddard, E.; Advances in Chemistry; American Chemical Society: Washington, DC, 31-52, 1968.
Teelmann K, Schlappi B, Schupbach M, Kistler A. Preclinical safety evaluation of intravenously administered mixed micelles. Arzneimittelforschung 1984,34:1517-23.
Toyama M. Next-Gen Liposuction. http://www.time.com/time/europe/forecast2003/html/liposuction.html, Dec. 8, 2002.
Victor S. Phosphatidylcholine works. Skin and Allergy News 2003, 34.
Womack et al., "Detergent Effects on Enzyme Activity and Solubilization of Lipid Bilayer Membranes", Biochimica et Biophysica Acta, 733, pp. 210-215 (1983).
Young, VL. Lipostabil: The effect of phosphatidylcholine on subcutaneous fat. Aesthetic Surg J 23:413-417,2003.
Restriction Requirement in U.S. Appl. No. 13/399,960 (dated Nov. 16, 2012).
Non-Final Office Action in U.S. Appl. No. 13/399,960 (dated Feb. 13, 2013).
Final Office Action in U.S. Appl. No. 13/399,960 (dated Oct. 22, 2013).
USPTO Decision on Appeal, U.S. Appl. No. 13/399,960 (Appeal No. 2015-001687), 19 pages (Mar. 16, 2017).
Non-Final Rejection in U.S. Appl. No. 15/653,483 (dated Oct. 30, 2017).
Final Rejection in U.S. Appl. No. 15/653,483 (dated Mar. 15, 2018).
"Evaluation of Safety and Efficacy of ATX-101 in the Reduction of Submental Fat," NCT01294644, Feb. 28, 2011.
Avissar et al., "Plasma Selenium-dependent Glutathione Peroxidase," J. Biol. Chem., (1989), 264(27):15850-15855.
Bril et al., "Fractionation of spinacho chloroplasts witn sodium deoxycholate," Biochim. Biophys. Acta, (1969), 172:345-348.
Chen et al., "Formation of Sodium Dodecyl Sulfate-stable Fibronectin Multimers," J Biol. Chem., (1996), 271 (15):9084-9089.
Cho et al.,"α-Lipoic Acid Inhibits Adipocyte Differentiation by Regulating Pro-adipogenic Transcription Factors via Mitogen-activated Protein Kinase Pathways," J. Biol. Chem, 2003, 278(37):34823-34833.
Complaint for Patent Infringement, *Kythera Biopharmaceuticals, Inc. v. Slayback Pharma LLC,* Filed Nov. 9, 2018.

(56) References Cited

OTHER PUBLICATIONS

Crowley et al., "The NAD+ precursors, nicotinic acid and nicotinamide protect cells against apoptosis induced by a multiple stress inducer, deoxycholate," Cell Death and Differentiation, (2000), 7:314-326.
Duncan et al., "Lipodissolve for subcutaneous fat reduction and skin retraction," Asethetic Surgery Journal, (2005), 25(5):530-543.
Extended European Search Report for Appl. No. 12747416.1, dated Jun. 10, 2014.
FDA Guidance for Industry, Q6B Specifications: Test Procedures and Acceptance Criteria for Biotechnological/Biological Products, U.S. Department of Health and Human Services Food and Drug Administration, Aug. 1999.
Gething et al., "Purification of fusion protein of Sendai virus: Analysis of the NH2-terminal sequence generated during precursor activation," Proc. Natl. Acad. Sci., (1978), 75(6):2737-2740.
Hofmann et al., "Physicochemical properties of bile acids and their relationship to biological properties: an overview of the problem," J. Lipid Res., (1984), 25:1477-1489.
Hofmann, et al., "Bile acid solubility and precipitation in vitro and in vivo: the role of conjugation, pH, and Ca2 ions," J Lipid Res., (1992), 33:617-626.
International Search Report and Written Opinion dated Jun. 29, 2012 in related PCT Application No. PCT/US2012/25719.
Lichtenberg et al., "On the solubility of calcium deoxycholate: kinetics of precipitation and the effect of conjugated bile salts and lecithin," Chem. Phys. Lipids, (1988), 46:279-291.
Lodish, et al. "Section 3.5—Purifying, Detecting and Characterizing Proteins," Molecular Cell Biology. 4th edition. New York: W. H. Freeman; 2000 pp. 83-99.
MacLachlan I., "Liposomal Formulations for Nucleic Acid Delivery," In Antisense Drug Technology, Principles, Strategies and Applications, 2nd Edition, Crooke S.T.; Ed.; Taylor & Francis Group, (2007), 237-270.
Mahler et al.,"Protein Aggregation: Pathways, Induction Factors, and Analysis," J. Pharm. Sci., (2009), 98(9):2909-2934.
Martins et al., "Lipid-based colloidal carriers for peptide and protein delivery—liposomes versus lipid nanoparticles," Int. J Nanomedicine, (2007), 2(4):595-607.
Murata et al., "Study of the Micelle Formation of Sodium Deoxycholate. Concentration Dependence of Carbon-13 Nuclear Magnetic Resonance Chemical Shift," J. Phys. Chem., (1982), 86:4690-4694.
Murata et al., "Study on the Micelle Formation of Sodium Deoxycholate, In Solution Behavior of Surfactants," Eds., Mittal K.L. et al., Plenum Press, New York, (1982), 611-627.
Narain, et al.,"Lecithin Protects against Plasma Membrane Disruption by Bile Salts," J. Surg. Res., (1998), 78(2):131-136.
Non-Final Office Action dated Dec. 21, 2018, in related U.S. Appl. No. 15/653,483.
Okuda, et al., "The Organic Composition of Earwax," J. Otolaryngol., (1991), 20(3):212-215.
Rotunda, AM, Suzuki H, Moy RL, Kolodney MS. Detergent effects of sodium deoxycholate are a major feature of an injectable phosphatidylcholine formulation used for localized fat dissolution. Dermatol Surg 30:1001-1008, 2004.
Ryden et al., "The effects of pH and bile salts on the binding of MelQx to wheat bran fibre," Mutation Res., (1996), 351:45-52.
Sachs et al., "The Effect of Pyrophosphate on the Amino Acid Incorporating System of Rat Liver Microsomes," J. Biol. Chem., (1958), 233(3):650-656.
Sigma Product Information Sheet, RIPA Buffer, Product No. R0278, Sep. 2003.
Sigma Product Information Sheet, Sodium deoxycholate,Product No. D6750, May 2006.
Small, D.M., Size and structure of bile salt micelles. Molecular Association in Biological and Related Systems Chapter 4. (1968), 31-52.
Smith, S. , "A Heated Debate on Hot Shot Fat-Zapper," The New York Post, Dec. 8, 2002, 12.
Stavroudis C., "Sorting Out Surfactants," WAAC Newsletter, (2009), 31(1):18-21.
Stoll et al., "In Vitro Dissolution and In Vivo Absorption of Nitrofurantoin from Deoxycholic Acid Coprecipitates," J Pharm. Sci., (1973), 62(1):65-68.
Su et al., "Regulation of System A Amino Acid Transport in 3T3-L1 Adipocytes by Insulin." J. Biol. Chem., (1998), 273(6):3173-3179.
Supplementary European Search Report from EP Patent Application No. 12 74 7416, dated Jun. 10, 2014.
U.S. Office Action dated Feb. 13, 2013 in related U.S. Appl. No. 13/399,960.
U.S. Office Action dated Nov. 16, 2012 in U.S. Appl. No. 13/399,960.
U.S. Office Action dated Oct. 22, 2013 in related U.S. Appl. No. 13/399,960.
U.S. Office Action dated Mar. 15, 2018 in U.S. Appl. No. 15/653,483.
Wendel, A., Lecithin: The First 150 Years—Part II: Evolution to a global pharmaceutical industry, Inform, (2000), 11:992-997.
Wright et al., "Formulation Development of AAV2 Vectors: Identification of Excipients That Inhibit Vector Aggregation," Mo. Therapy, (2004), 9(Supplement 1):S163, Abstract 425.
Zhang et al., "A potent small molecule inhibits polyglutamine aggregation in Huntington's disease neurons and suppresses neurodegeneration in vivo," Proc. Natl. Acad. Sci., (2005), 102(3):892-897.
Humphrey S et al. Mar. 21, 2011. ATX-101 for reduction of submental fat: A Phase II Randomized Controlled Trial. Dermatologic Surgery 75(4), 788-797.

\* cited by examiner

| Score | Description | Oblique view | Frontal view | Profile view |
|---|---|---|---|---|
| 0 | Absent submental convexity: No localized submental fat evident | | | |
| 1 | Mild submental convexity: Minimal, localized submental fat | | | |
| 2 | Moderate submental convexity: Prominent, localized submental fat | | | |
| 3 | Severe submental convexity: Marked, localized submental fat | | | |
| 4 | Extreme submental convexity | | | |

FIG. 3

TREATMENT OF SUBMENTAL FAT

CROSS REFERENCE TO RELATED APPLICATIONS

This application is a continuation of U.S. patent application Ser. No. 13/399,960, filed Feb. 17, 2012, which claims the benefit under 35 U.S.C. § 119(e) of U.S. Provisional Application No. 61/444,613, filed Feb. 18, 2011, the entire contents of both of which are incorporated herein by reference.

FIELD OF THE DISCLOSURE

This disclosure relates to methods for non-surgical reduction of localized subcutaneous fat such as that associated with a cosmetic fat accumulation. The methods employ compositions having specific concentrations of a salt of deoxycholic acid which provides a superior fat cell necrosis with modest adverse effects. In one embodiment, the localized subcutaneous fat is found in the submental area, in particular under the chin.

BACKGROUND

Fat accumulation under the chin is a unique phenomenon, which can often occur in individuals who are not otherwise overweight. This area around the neck can be resistant to weight reduction measures, with liposuction being the primary intervention. Deoxycholic acid or a salt thereof represents a promising nonsurgical treatment for unwanted submental fat deposition.

Any assessment of the risks and benefits of a proposed therapy should necessarily consider the risks and benefits of alternative treatments. In the case of deoxycholic acid for the reduction of subcutaneous (SC) fat in the submental area, there are no approved or rigorously evaluated nonsurgical alternatives. Surgical alternatives include, on a scale of increasing invasiveness, various forms of liposuction up to neck reconstruction. All surgeries are associated with the known risks of anesthesia, infection, bleeding, bruising, and scarring, as well as the possibility of poor outcome and the expected discomfort and "down-time" for the patient.

Presently, mixtures of phosphatidylcholine (PC) and deoxycholate (DC), which are not approved by the United States (US) Food and Drug Administration (FDA), have been used in increasing frequency to reduce the size of localized deposits of fat. Perhaps most relevant, Lipostabil® (5% PC and 4.75% DC) and extemporaneous, pharmacy-compounded mixtures of PC and DC (PC/DC) have found increasing use in the treatment of unwanted fat deposits for cosmetic purposes. Many US physicians and aesthetic clinics currently use various unapproved formulations of PC/DC prepared by compounding pharmacies for administration in uncontrolled environments.

In spite of these risks, the growing appeal of cosmetic medical treatment of these procedures is a testament to the psychological importance of body image and the beneficial outcomes of these procedures, as perceived by the patients who seek them.

SUMMARY

This disclosure provides compositions, kids, and treatment schedules and methods of effectively removing localized subcutaneous fat. Such fat is sometimes referred to herein as "cosmetic fat" in that the so treated fat is not pathogenic in nature. An example of such cosmetic fat is the fat deposited in the submental area of a human patient, referred to as "submental fat (SMF)."

Thus, one embodiment of the present disclosure provides a non-surgical method for the reduction of submental fat in a subject, said method comprising a plurality of subcutaneous injections of a solution of deoxycholic acid or a salt thereof into said submental fat, each injection of said plurality administering about 1 mg to about 2 mg of said deoxycholic acid or salt thereof per square centimeter of the skin area over said submental fat. In one aspect, the sites for injection are at least about 1 cm apart from each other.

Another embodiment of the present disclosure provides a method for decreasing a submental fat deposit under a skin area in a human subject, which method comprises local injection to the submental fat deposit, through a plurality of spots on the skin area, a composition comprising an effective amount of a salt of deoxycholate, wherein the effective amount is from about 1 mg to about 2 mg per square centimeter of the skin area.

Also provided is a method for decreasing a submental fat deposit in a human subject which method comprises measuring the thickness of the submental fat deposit to be decreased; marking, on skin proximate to the submental fat deposit, a grid comprising a plurality of spots, each of which is from about 0.8 cm to about 1.2 cm distant from an adjacent spot of the grid; and injecting, with a suitable needle, through each of the plurality of spots, into about half way into the submental fat deposit, an effective amount of a composition comprising from about 0.5% to about 1% (w/w) of a salt of deoxycholate, wherein each injection constitutes delivery of from about 0.1 mL to about 0.3 mL of the composition.

Yet another embodiment provides a method for decreasing a submental fat deposit in a human subject which method comprises measuring the thickness of the submental fat deposit to be decreased; marking, on skin proximate to the submental fat deposit, a grid comprising about 40-60 spots, each of which is from about 1 cm distant from another spot of the grid; and injecting, with a suitable needle, through each of the spots, into about half way into the submental fat deposit, an effective amount of a composition comprising about 1% (w/w) of a salt of deoxycholate, wherein each injection constitutes delivery of about 0.2 mL of the composition.

These and other aspects of the disclosure will be further described in details below.

BRIEF DESCRIPTION OF THE DRAWING

FIG. 3 presents an exemplary score card to be used for evaluating the grade of submental fat in a patient.

DETAILED DESCRIPTION OF THE DISCLOSURE

Definitions

Figure 1:
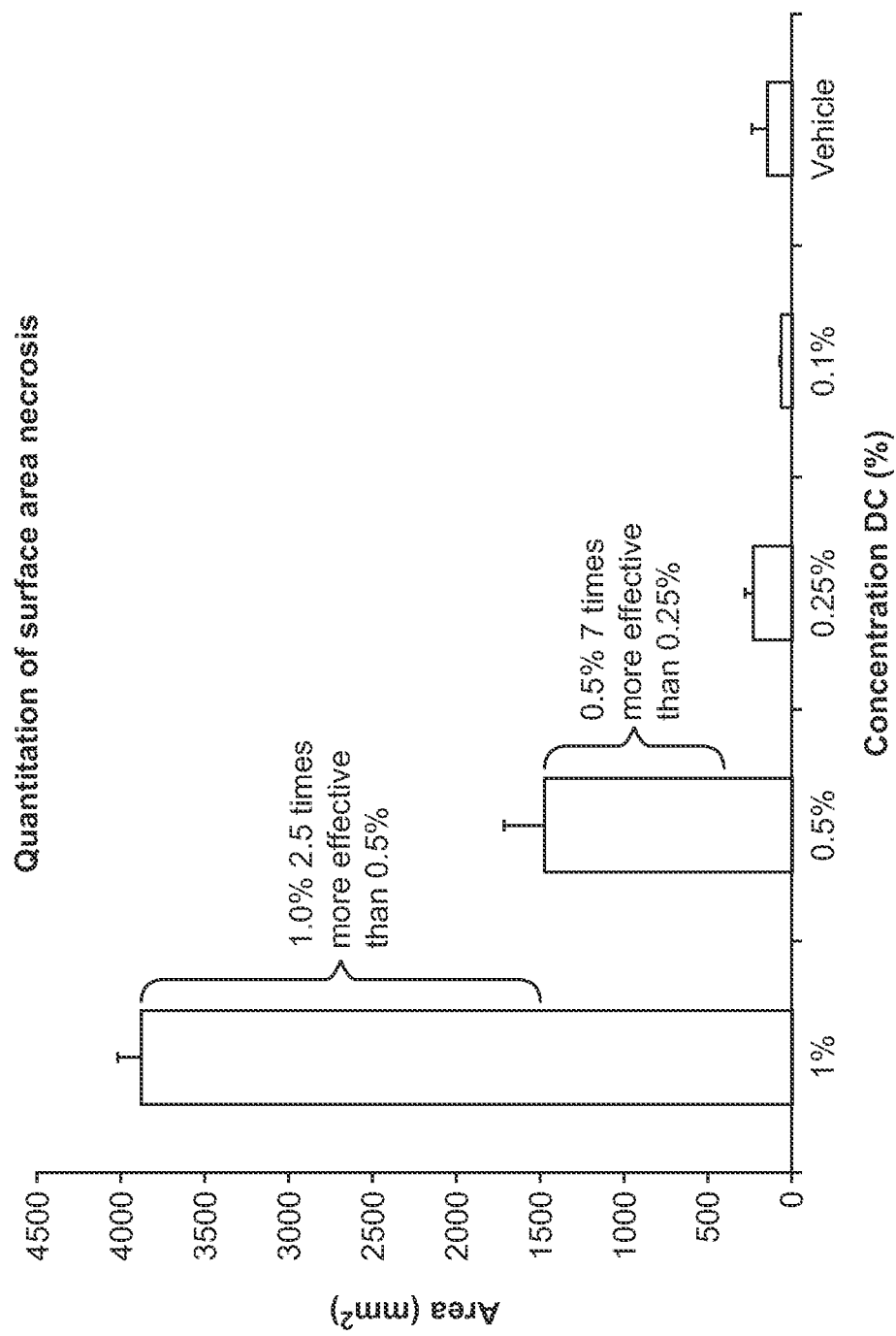
FIG. 1 provides quantitation of fat pad surface area necrosis in Zucker rats treated with varying concentrations of deoxycholic acid.

Throughout this disclosure, various publications, patents and published patent specifications are referenced by an identifying citation. The disclosures of these publications, patents and published patent specifications are hereby incorporated by reference into the present disclosure to more fully describe the state of the art to which this disclosure pertains.

As used herein, certain terms may have the following defined meanings. As used in the specification and claims, the singular form "a," "an" and "the" include singular and plural references unless the context clearly dictates otherwise.

As used herein, the term "comprising" is intended to mean that the compounds and methods include the recited elements, but not excluding others. "Consisting essentially of" when used to define compositions and methods, shall mean excluding other elements of any essential significance to the compounds or method. "Consisting of" shall mean excluding more than trace elements of other ingredients for claimed compounds and substantial method steps. Embodiments defined by each of these transition terms are within the scope of this disclosure. Accordingly, it is intended that the methods and compounds can include additional steps and components (comprising) or alternatively include additional steps and compounds of no significance (consisting essentially of) or alternatively, intending only the stated methods steps or compounds (consisting of).

The term "pharmaceutically acceptable salt" or simply "salt" refers to pharmaceutically acceptable salts of deoxycholic acid, which salts are derived from a variety of organic and inorganic counter ions well known in the art and include, by way of example only, lithium ($Li^+$), sodium ($Na^+$), potassium ($K^+$), calcium ($Ca^{2+}$), magnesium ($Mg^{2+}$), ammonium ($NH_4^+$), and tetraalkylammonium ($NR_4^+$), wherein each R is independently an alkyl group having from 1 to 4 carbon atoms). In one embodiment, the salt employed is sodium ($Na^+$).

The term "pharmaceutically acceptable excipient" refers to a compound that is useful in preparing a pharmaceutical composition that is generally safe, non-toxic and neither biologically nor otherwise undesirable, and includes excipients that are acceptable for human pharmaceutical use or veterinary use. A pharmaceutically acceptable excipient as used in the specification and claims includes both one and more than one such excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, methyl cellulose, lubricating agents such as talc, magnesium stearate, and mineral oil; wetting agents; emulsifying and suspending agents; and preserving agents such as methyl- and propylhydroxy-benzoates and benzyl alcohol. The compositions of the present disclosure can be formulated so as to provide quick, sustained or delayed release of the active ingredient after administration to the patient by employing procedures known in the art.

The term "pharmaceutically acceptable buffer" when used herein refers to conventional buffers heretofore used in aqueous pharmaceutical compositions which are able to resist a change in pH when $H^+$ or $OH^-$ is added. A buffering agent can be a single compound or a combination of compounds. Examples pharmaceutically acceptable buffers include, without limitation, solutions of sodium phosphate, potassium phosphate, disodium hydrogenphosphate, dipotassium hydrogen phosphate, sodium dihydrogen phosphate, potassium dihydrogen phosphate, phosphoric acid, for example, phosphate buffered saline. A preferred buffer is sodium phosphate.

The term "about" when used before a numerical value indicates that the value may vary within reasonable range, such as ±10%, ±5%, and ±1%.

The term "remove", "removal", "reduce" or "reduction" of a localized subcutaneous fat deposit means to decrease the size, volume, or thickness of the fat deposit.

The term "cosmetic" as it relates to fat deposit refers to fat deposits which are neither pathological in nature nor which form a solid mass capable of growth such as lipomas which can grow to as large as 10 centimeters in diameter. Such cosmetic conditions are viewed by the patient as merely unsightly and not disease related. Included in the cosmetic conditions are fat deposits in the submental area resulting in a "double chin". That is to say a subcutaneous fat deposit around the neck that sags down and creates a wrinkle, making the owner appear to have a second chin. Other subcutaneous fat deposits which are cosmetic in nature include fat accumulations in the lower eyelid, under the arm, on the waist, hips and other cosmetic areas.

The term "subject" refers to a human who is desired to reduce his or her localized fat from a specific area, for example under the chin.

Methods

Various embodiments of the present disclosure provide methods for decreasing submental fat deposit under a skin area in a human subject, for enhancing the cosmetic appearance of a human patient, or for providing a facial cosmetic benefit to a human subject. In one embodiment, such methods are non-surgical and do not include liposuction.

The submental fat deposit treated by the methods of this disclosure, in one aspect, is cosmetically unappealing but is non-pathological and the reduction of it is to improve the appearance of the subject, for example, by reducing the appearance of a double chin.

One embodiment of the present disclosure provides a non-surgical method for the reduction of submental fat in a subject, said method comprising a plurality of subcutaneous injections of a solution of deoxycholic acid or a salt thereof into said submental fat, each injection of said plurality administering about 1 mg to about 2 mg of said deoxycholic acid or salt thereof per square centimeter of the skin area over said submental fat.

In alternative embodiments, each rejection comprises at least about 1.1, 1.2, 1.3, 1.4, 1.5, 1.6, 1.7, 1.8 or 1.9 mg of the deoxycholic acid or salt thereof per square centimeter of the skin area. In another embodiment, each rejection comprises no more than about 1.9, 1.8, 1.7, 1.6, 1.5, 1.4, 1.3, 1.2 or 1.1 mg of the deoxycholic acid or salt thereof per square centimeter of the skin area.

In some aspects, the sites for injection are at least about 1 cm apart from each other. In alternative embodiments, such distance is from about 0.9 cm to about 1.1 cm, or from about 0.8 cm to about 1.2 cm, from about 0.7 cm to about 1.3 cm, from about 0.6 cm to about 1.4 cm, or from about 0.5 cm to about 1.5 cm.

In one embodiment, provided is a method for decreasing a submental fat deposit under a skin area in a human subject, which method comprises local injection to the submental fat deposit, through a plurality of spots on the skin area, a composition comprising an effective amount of deoxycholate or a salt thereof, wherein the effective amount is from about 0.01 mg to about 1 mg per square centimeter of the skin area.

In some aspects, the composition that comprises deoxycholate of a salt thereof is also referred to as a "deoxycholate composition," more details of which are provided in this disclosure below.

In one aspect, the effective amount is at least about 0.02, 0.05, 0.1, 0.15, 0.2, 0.3, 0.4, 0.5 or 1 mg per square centimeter of the skin area. In another aspect, the effective amount if no more than about 0.1, 0.2, 0.3, 0.4, 0.5, 0.6, 0.7, 0.8, 0.9 or 1 mg per square centimeter of the skin area.

In one aspect, the plurality of spots are substantially evenly distributed on the skin area. The term "substantially evenly" as used here, refers to spots in an area where there are substantially the same number of spots per unit of area. In one aspect, a number is substantially the same as another number is they are with about 5% or 10%, or 15% or 20%, or 25% difference.

In another aspect, each spot is from about 0.8 cm to about 1.2 cm distant from an adjacent spot. In yet another aspect, each spot is from about 0.9 cm to about 1.1 cm distant from an adjacent spot. In still another aspect, each spot is about 1 cm distant from an adjacent spot.

In some aspects, the plurality of spots comprises at least 20 spots, or alternatively at least 25, 30, 35, 40, 45, 50, 55, 60, 70, 80, 90, or 100 spots. In some aspects, the plurality of spots consists of no more than about 100, 90, 80, 70, 60, 50, 45, 40, 35, 30, or 25 spots. In a particular aspect, the plurality of spots consists of from about 40 to about 60 spots, or about 50 spots.

In one aspect, each spot receives from about 0.005 mL to about 0.1 mL of the composition. In an alternative aspect, each spot receives from about 0.01 mL to about 0.05 mL, or alternatively from about 0.01 to about 0.03, or from about 0.015 to about 0.025 mL of the composition. In a particular aspect, each spot receives from about 0.02 mL of the composition.

In another embodiment, the present disclosure provides a method for decreasing a submental fat deposit in a human subject which method comprises, measuring the thickness of the submental fat deposit to be decreased; marking, on skin proximate to the submental fat deposit, a grid comprising a plurality of spots, each of which is from about 0.8 cm to about 1.2 cm distant from an adjacent spot of the grid; and injecting, with a suitable needle, through each of the plurality of spots, into about half way into the submental fat deposit, an effective amount of a composition comprising from about 0.5% to about 1% (w/w) of a salt of deoxycholate, wherein each injection constitutes delivery of from about 0.1 mL to about 0.3 mL of the composition.

In one aspect, the thickness of the submental fat deposit is measured with magnetic resonance imaging (MRI) or by a caliper.

In one aspect, the needle is positioned about half-way through the fat deposit before the injection is initiated. In another aspect, the needle has a length that is about half of the thickness.

In some aspects, the grid comprises at least 20 spots, or alternatively at least 25, 30, 35, 40, 45, 50, 55, 60, 70, 80, 90, or 100 spots. In some aspects, the grid comprises no more than about 100, 90, 80, 70, 60, 50, 45, 40, 35, 30, or 25 spots. In a particular aspect, the grid comprises from about 40 to about 60 spots, or about 50 spots.

Figure 25:
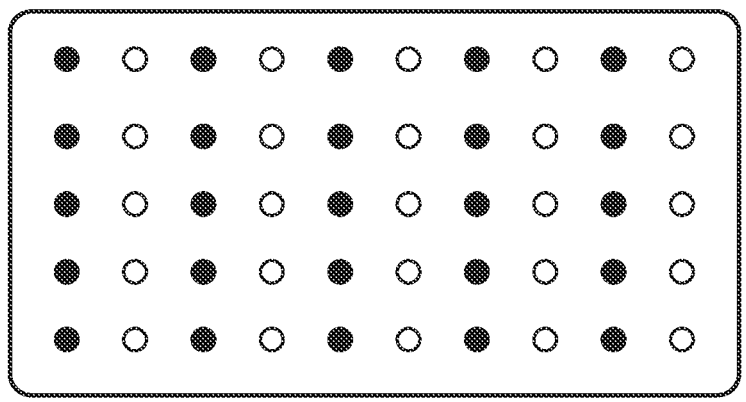
FIG. 25 illustrates a tattoo useful for applying a 5×10 grid on the chin of a subject.

In some aspects, the grid is marked by applying a tattoo, printed with the grid, as illustrated in FIG. 25, to the skin.

In one aspect, the steps of marking and injecting are repeated for at least 3 times. In another aspect, steps of marking and injecting are repeated for 4 times. In another aspect, steps of marking and injecting are repeated for 6 times. In another aspect, steps of marking and injecting are repeated for 7, or 8 or 9 times. In some of the above aspects, each repeat is from about 3 days to about 7 days, or about 6 days, or about 5 days, or about 4 days apart.

In some aspects, the methods further comprise pretreating the area around the injection sites with a local anesthetic.

In any of the above embodiments, the methods can further include steps of ascertaining the effectiveness of the method. In one aspect, the steps include, before and after the treatment, identifying a first score and a second score, respectively, for the localized submental deposit, using a score card comprising a plurality of images each depicting a localized submental deposit of a different size and determining that the therapy is effective in reducing the localized submental deposit if the second score differs from the first score in a direction reflecting a reduction in size of the localized submental deposit.

Also provided, in one embodiment, is a method for ascertaining the effectiveness of a therapy for reducing a localized submental deposit in a patient, which method comprises identifying a first score for a localized submental deposit in a patient, using a score card comprising a plurality of images each depicting a localized submental deposit of a different size; administering to the patient a therapy; identifying a second score for the submental deposit in the patient using the score card; and determining that the therapy is effective in reducing the localized submental deposit if the second score differs from the first score in a direction reflecting a reduction in size of the localized submental deposit.

Still also provided, in one embodiment, is a method for reducing a localized submental deposit in a patient, which method comprises: identifying a score for a localized submental deposit in a patient, using a score card comprising a plurality of images each depicting a localized submental deposit of a different size; and administering to the patient an effective amount of a therapy for reducing a localized submental deposit, wherein the amount of the therapy is determined on the score.

In one aspect, the localized fat is reduced by at least 10% of the volume, or by at least 10% of its thickness, as determined by MRI or by caliper measurement. The % of the volume reduction is determined by subtracting the volume after treatment (volume after treatment: Vf) and that of the baseline (initial volume or volume before treatment: Vi), divided by Vi and multiplied by 100. Similarly the % of the thickness reduction is determined by subtracting the thickness after treatment (thickness after treatment: Tf) and that of the baseline (initial volume or volume before treatment: Ti), divided by Ti and multiplied by 100. As an example to determine percentage reduction in volume, if Vi is 6346.8 cc, Vf is 5376.6 cc, then the volume is reduced by 18%. Similarly to determine percentage reduction in thickness, if Ti is 17.2 mm, Tf is 14.1 mm, then the thickness is reduced by 15%. In another aspect, the lessening of the double chin appearance can be determined by CR-SMFRS, RS-SMFRS, or PRSMFIS, or combinations thereof, using the CR-SMF scale, which is copyrighted by Kythera Pharmaceuticals, Inc., incorporated herein by reference. The lessening of the double chin appearance may be determined by the improvement in the degree of the submental convexity of the area under the chin as described in the CR-SMF scale. The double chin appearance is improved when the CR-SMFRS is determined to be changed by at least 1 grade (for example, from grade 3, which is prior to treatment, to grade 2 after treatment).

In some embodiments, the reduction of submental fat enhances the facial appearance of said subject. In one aspect, the enhanced facial appearance is due to the reduced appearance or the lack of the double-chin display.

In one aspect of any of the above embodiment, the reduction is determined by at least a physical measurement and/or reading from a scale. In one aspect, the physical measurement comprises MRI and/or caliper.

In one aspect, the submental fat is reduced in thickness and/or volume as determined by MRI.

In some aspects, the thickness and/or volume is reduced by at least about 10%, or by at least about 15%, 20%, 25%, 30%, 35%, 40%, 45%, or 50%.

In one aspect, the scale is selected from the group consisting of: CR-SMFRS, RS-SMFRS, PRSMFIS, and any combinations thereof.

In one aspect, the facial appearance is enhanced by at least 1 grade, or at least 2 grades. In some aspects, the facial appearance is enhanced by at least 1 grade or 2 grades, as determined by CR-SMFRS.

In one aspect, the enhancement is achieved within 8 weeks from the injection. In some aspects, the enhancement is achieved within about 12, 11, 10, 9, 7, 6 or 5 weeks from the injection.

In one aspect, the facial appearance is enhanced by at least 2 grades, as determined by CR-SMFRS. The CR-SMFRS can be determined, for instance, with a score card as shown in FIG. 3 and further described below.

In any of the above embodiments, the volume for each injection is about 0.1 ml to about 0.2 ml.

In one aspect, the deoxycholic acid or salt thereof is in an aqueous solution buffered at a pH of between about 8.0 and about 8.5.

In some aspects, the total of said deoxycholic acid or salt thereof administered is between about 50 mg to about 100 mg, or from about 60 mg, 70 mg to about 90 mg, 80 mg, without limitation.

Figure 2:
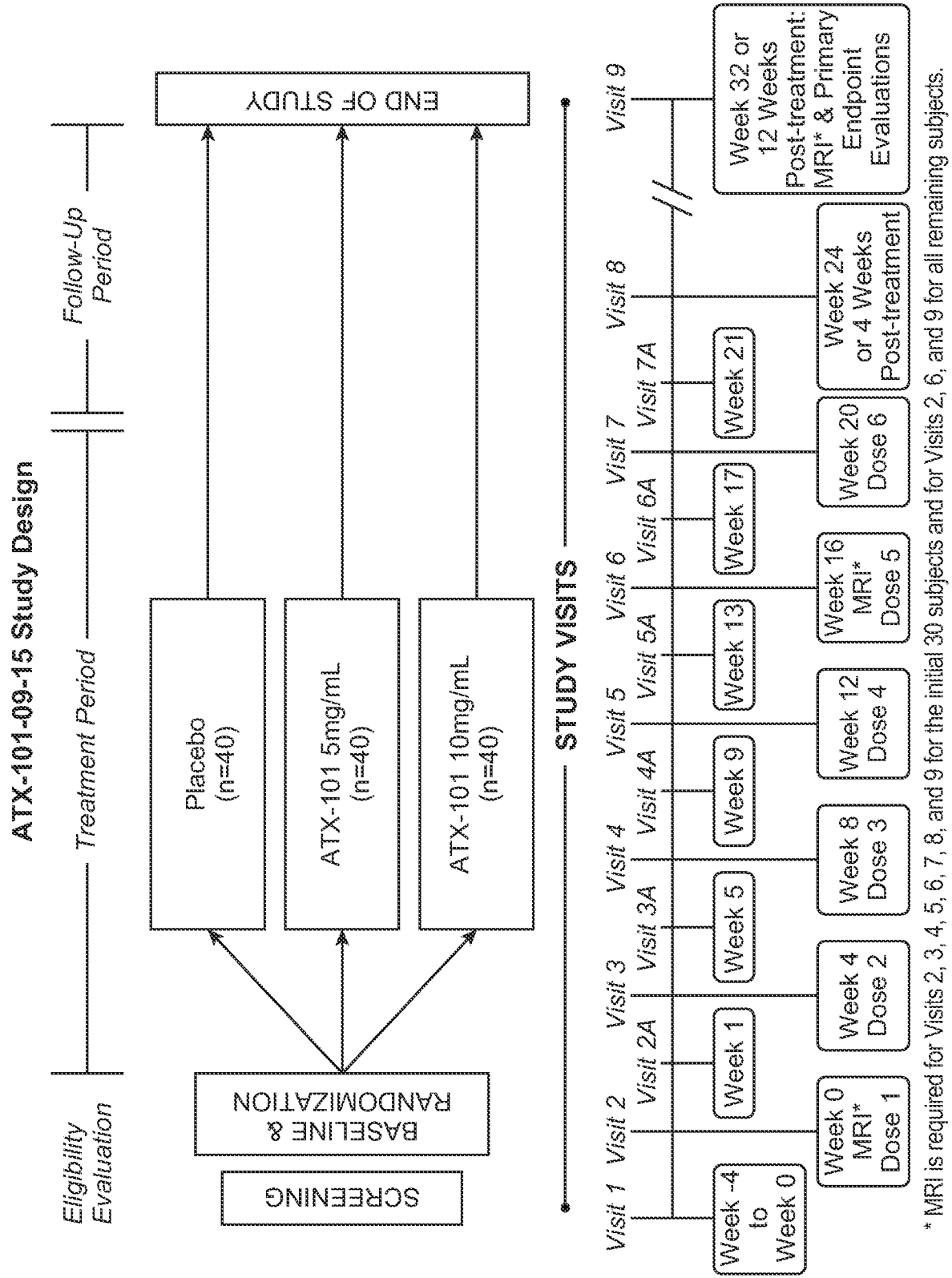
FIG. 2 depicts the study design and treatment schema used in Example 3.

In one aspect, the treatment is performed in a plurality of visits by the subject, the plurality of visits are according to the schedule shown in FIG. 2.

The deoxycholic acid, in some aspects, is biologically derived or de novo synthesized. In one aspect, the deoxycholic acid is animal derived. In another aspect, the deoxycholic acid is de novo synthesized and wherein the solution comprising thereof is free of primary bile acids and/or other secondary bile acids. In another aspect, the primary bile acid is cholic acid. In some aspects, the solution further comprises benzyl alcohol at a concentration of about 0.8% to about 1%.

In some aspects, the method comprises co-administering an agent selected from the group consisting of: anesthetic, anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents, or any combinations thereof. In one aspect, the co-administering is prior to, at the same time, or following the said plurality of injection.

In one aspect, the injection further comprises a lipase. In another aspect, the injection further comprises a phospholipid. In yet another aspect, the phospholipid comprises phosphatidylcholine.

The ratio of the deoxycholic acid or salt thereof and the phosphatidylcholine, in one aspect, is about 1:0.005, about 1:0.05, or about 1:0.5.

Score Cards

Score cards, as illustrated in FIG. 3, are provided in the present disclosure. Such score cards are useful for evaluating the treatment effects and/or provide basis for determining treatment schedule.

In one embodiment, the present disclosure provides a score card for measuring the effectiveness of a therapy for reducing a localized submental deposit in a patient, which score card comprises a plurality of images, each image depicting a subject showing a localized submental deposit of a different size, wherein each image is annotated with a score indicating the size of the localized submental deposit.

In some aspects, the score card in an electronic form or a printed form. Exemplary images on the score card include, without limitation, photographs, magnetic resonance images or sketches.

In one aspect, the score card comprises, for each score, two of more images showing the localized submental deposit of the corresponding size, each from a different angle and/or from a different subject.

In another aspect, the score card comprises 4, 5, 6, or 7 different scores, each being an integer. In some aspects, the score card also includes a descriptive text for each score.

A particular embodiment of the present disclosure provides a score card for measuring the effectiveness of a therapy for reducing a localized submental deposit in a patient, which score card comprises from 4 to 6 groups of images, wherein each group is annotated with a score indicating the size of a localized submental deposit, each images depicts a subject showing a localized submental deposit, and the localized submental deposits shown in each group correspond to the score of the group, wherein each image in each group shows the localized submental deposit from a different angle and/or from a different subject.

Kits

Kits are also provided, which can facilitate treatment methods of the present disclosure in a clinical setting, without limitation. In one aspect, the kit includes a tattoo configured to mark a grid on a skin, the grid comprising a plurality of spots, each of which is from about 0.8 cm to about 1.2 cm from a closest spot of the grid; an effective amount of a composition comprising from about 0.5% to about 1% (w/v) of a salt of deoxycholate; and a plurality of syringes and needles.

In some aspects, the kits further include a score card of the present disclosure.

Deoxycholate Compositions

In one embodiment, a deoxycholate composition comprises from about 0.5 weight percent to less than 2 weight percent of a pharmaceutically acceptable salt of deoxycholic acid and a pharmaceutically acceptable excipient. In another aspect of the embodiment, the composition comprises about 0.5 weight percent or about 1 weight percent of sodium deoxycholate.

In another embodiment, the composition comprises from about 0.5 weight percent to less than 2 weight percent of a pharmaceutically acceptable salt of deoxycholic acid, a phospholipid at a concentration which is greater than, equal to, or less than the concentration of the sodium deoxycholate and a pharmaceutically acceptable excipient. For example, the mass ratio of sodium deoxycholate and phospholipids may be 1:0.5, 1:0.05, 1.005, etc. In some embodiments, the concentration of the phospholipids (e.g., phosphatidylcholine) in % w/v is less than the concentration of % w/v of the detergent(s). For example, a composition may have about 1% w/v sodium deoxycholate and less than about 1% w/v phosphatidylcholine. Less than about 1% of phosphatidylcholine includes about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, etc., including the range spanning between any aforementioned two successive numbers.

In another aspect, the composition comprises either about 0.5 or 1 weight percent of a pharmaceutically acceptable salt of deoxycholic acid and a buffer to maintain the pH at about 8 to about 8.5.

In some embodiments, the composition comprises about 0.6%, about 0.7%, about 0.8%, about 0.9% or about 1.0% w/w (weight/weight), or w/v (weight/volume) of the salt of deoxycholic acid. In one embodiment, the pharmaceutically acceptable salt of deoxycholic acid is the sodium salt.

In some embodiments, the composition used in the methods of this disclosure is essentially free of phosphatidylcholine. The term "essentially free of phosphatidylcholine" refers to less than 1% w/w of phosphatidylcholine in the composition, or less than 0.5% w/w. In some embodiments, the composition is free of phosphatidylcholine.

In some embodiments, the deoxycholic acid or the pharmaceutically acceptable salt thereof is synthetic. Each of U.S. Patent Application Publication Nos. 2008/0318870 and 2009/0270642, U.S. Provisional Patent Application No. 61/303,816, as well as International Patent Application No. PCT/US10/61150 describes procedures of preparing synthetic deoxycholic acid or a pharmaceutically acceptable salt thereof, are incorporated by reference in their entirety.

In some embodiments, the synthetic deoxycholic acid or the pharmaceutically acceptable salt thereof has a purity of at least 99%. U.S. Provisional Patent Application No. 61/288,132 as well as International Patent Application No. PCT/US10/61150, which discloses methods of preparing synthetic deoxycholic acid or a pharmaceutically acceptable salt having a purity of at least 99%, is incorporated by reference in its entirety.

In some embodiments, the composition used in the methods of this disclosure further comprises benzyl alcohol. In some embodiments, the benzyl alcohol is about 0.8 to about 1% w/w. In some embodiments, the concentration of benzyl alcohol is about 0.9% w/w.

In some embodiments, the composition used in the methods of this disclosure further comprises an effective amount of a pharmaceutically acceptable buffer to maintain the pH of the composition at about 8 to 8.5, for example, 8.3. In some embodiments, the buffer is phosphate buffered saline.

In some embodiments, the composition used in the methods of this disclosure a composition comprises either about 0.5 or about 1 weight percent of sodium deoxycholate, about 0.8 to 1 weight percent benzyl alcohol and an effective amount of a pharmaceutically acceptable buffer to maintain the pH of the composition at about 8 to 8.5, wherein said composition is essentially free of phosphatidyl choline.

In some embodiments, the compositions can further comprise a second therapeutic agent selected from the group consisting of: anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents.

The composition is an injectable solution and comprises a pharmaceutically acceptable excipient which is an aqueous carrier, examples of which include water, saline, aqueous dextrose.

In some embodiments, the composition is in a container that contains up to 500 mL of solution. Such container can be a syringe or syringe-loadable container.

Unit Doses

In another aspect, this invention provides a unit dose of a composition for non-surgical, in particular, cosmetic, reduction of a localized subcutaneous fat deposit in a patient having such a deposit and desiring to reduce such a deposit, which unit dose comprises about 25 mL of a sterile aqueous solution containing either about 0.5% or about 1% w/w of a salt of deoxycholic acid. In some embodiments, the aqueous solution is a composition as described above. The total dosage for a treatment according to the instant invention is between 200 mg to about 1000 mg of sodium deoxycholate, in particular, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg.

It is understood that the unit dose represents the maximum amount of the composition to be injected in a single treatment regimen using multiple injections. That is to say that if a single treatment regimen constitutes 50 injections with each injection being limited to 0.2 mL of the aqueous composition then the unit dose is 10 mL of the composition. In a preferred embodiment, the unit dose is the amount of the composition maintained in a single container such as a vial or a syringe.

In some embodiments, the unit dose is an aqueous composition of sodium deoxycholate.

In some embodiments, the unit dose is repeatedly administered in treatment sessions to the patient until the desired reduction in subcutaneous fat is reached. In some embodiments, 4, 5 or 6 treatment sessions can be conducted during a 4 week period which may be varied with plus or minus 5 days.

In some embodiments, the unit dose is contained in a syringe for a single subcutaneous injection.

EXPERIMENTAL EXAMPLES

Example 1

This example presents in vitro and in vivo studies showing that sodium deoxycholate solutions, at a concentration at or above 0.5% and below 2%, are both effective and safe in inducing fat cell necrosis resulting in reduced fat accumulation.

In vitro studies indicated that 0.25% w/v sodium deoxycholate is the minimal concentration at which micelle formation was observed. When secreted into the small intestine, bile acids form micelles with dietary fats to aid in lipolysis and lipid absorption.

Data from an in vivo Zucker rats and clinical studies that employed doses of 0.5% and 1.0% w/v DCA determined that these concentrations were effective, while doses at and below 0.25% are no different than vehicle (FIG. 1). In the rats study, 8 rats received a single injection into the caudal lateral fat pads of 2.5 mL deoxycholic acid at 1%, 0.5%, 0.25%, or 0.1% concentrations, or 2.5 mL vehicle (0.9% benzyl alcohol in water). Examination of the fat pads showed that when necrosis occurred, it was through the entire fat pad and was visible on the back (non-skin) side. The data from this study show that 1.0% deoxycholic acid caused approximately 2.5 times more necrosis than 0.5%, and that the deoxycholic acid concentrations that were below the critical level to form micelles (≤0.25%) did not result in fat necrosis.

Concentrations of 2.0% and 4.0% were shown by clinical trial to be associated with marked necrosis, resulting in lipid lake formation and vessel damage, which might reduce or delay macrophage and fibroblast migration into the necrotic tissue. The observed histological changes may explain the decreased efficacy with the higher concentrations of deoxycholic acid (2.0% and 4.0%) at the earlier time points. These findings are consistent with the increased intensity of adverse effects at the higher concentrations and larger volumes administered (0.4 mL/injection) in clinical trials. In contrast, a better clinical efficacy and safety profile was observed at the lower concentrations (0.5% and 1.0%), which may be attributed to the more rapid resolution of the histological changes. Concentrations at or below 0.25% were not tested, as they are at or below the concentration necessary to form micelles. The formation of micelles is essential for lipolytic activity.

Example 2

This example present the procedure and results of a clinical study, showing that sodium deoxycholate solutions, at a concentration at or above 0.5% and below 2%, demonstrated superior results, in removing submental fat deposits in human patients, as compared to concentrations beyond this range.

A clinical study was conducted to evaluate the effectiveness of various doses of sodium deoxycholate in removing undesired submental fat (SMF) deposits. A multicenter, randomized, double-blind, placebo-controlled, parallel-group comparison of 3 concentrations of sodium deoxycholate (0.5, 1.0, and 2.0 percent w/v) in sterile water with 0.9% benzyl alcohol and placebo was conducted to determine the efficacy of reduction in SMF deposits. Placebo injection consisted of sterile water with 0.9% benzyl alcohol.

All subjects were to have up to 4 treatment sessions at intervals of no less than 4 weeks (±3 days) between treatments.

Eligible subjects were concurrently randomized into one of the following groups:
  Placebo injected every 4 weeks for up to 4 treatments
  0.5% w/v sodium deoxycholate injected every 4 weeks for up to 4 treatments
  1.0% w/v sodium deoxycholate injected every 4 weeks for up to 4 treatments
  2.0% w/v sodium deoxycholate injected every 4 weeks for up to 4 treatments 85 subjects were randomized: 21 subjects to the 0.5% w/v sodium deoxycholate group, 20 subjects to the 1.0% w/v sodium deoxycholate group; 22 subjects to the 2.0% w/v sodium deoxycholate (DCA) group; and 22 subjects to the placebo group. 73 subjects completed the study.

Subject selection included males or non-pregnant, non-lactating females aged 25 to 65 years, inclusive, on the date of randomization, with SMF that was considered undesirable by the subject and graded by the investigator as 2 or 3 using the SMF rating scale, and a history of maintenance of a stable body weight, in the judgment of the investigator, for at least 6 months before randomization.

The baseline SMF rating scale score was similar across all treatment groups. At week 16, changes from the baseline were observed for all treatment groups, including placebo. The ANCOVA (parametric analysis of covariance) analysis showed that the change from baseline at week 16 compared to placebo in SMF rating scale score was statistically significant for the 0.5% w/v DCA (P=0.043; 95% CI for least squares mean [LSM] difference: −0.9, 0.0) and for 1% w/v DCA (P=0.050; 95% CI for LSM difference: −0.8, 0.0) treated groups but not for the 2% w/v DCA treated group.

Figure 23:
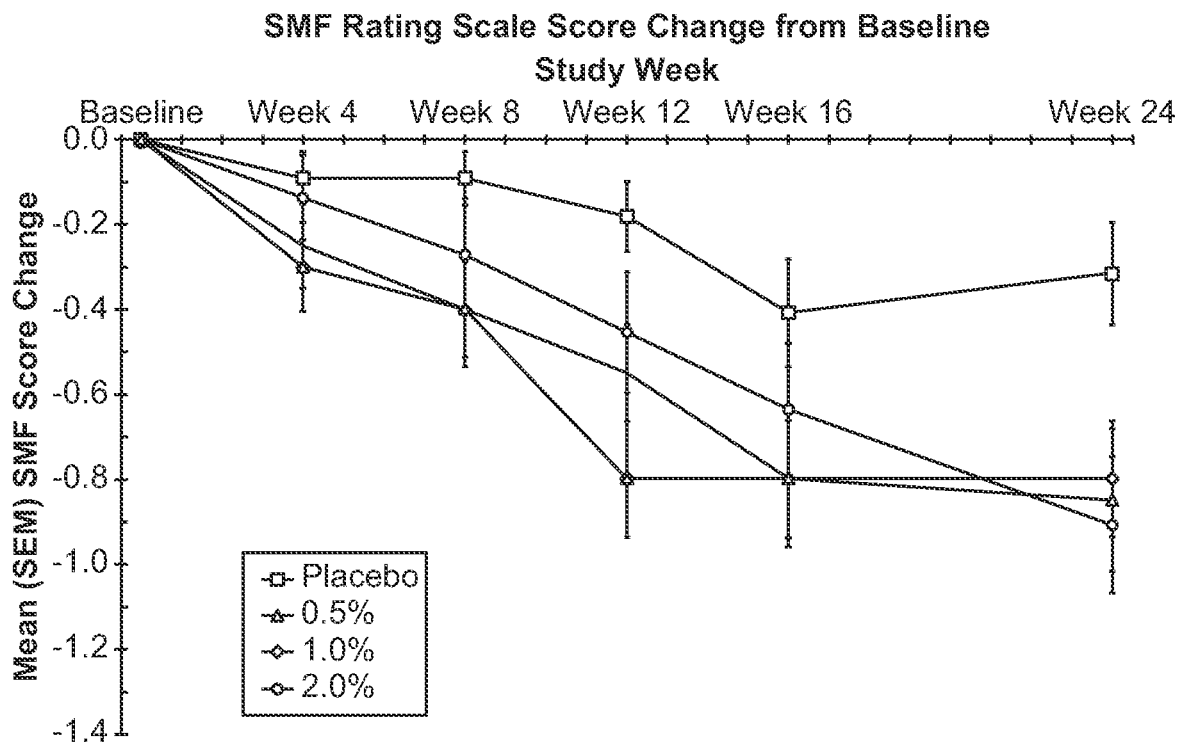
FIG. 23 compares the effectiveness among ATX-101 0.5%, 1.0% and 2.0% with the mean SMF score changes at different time points.
Figure 24:
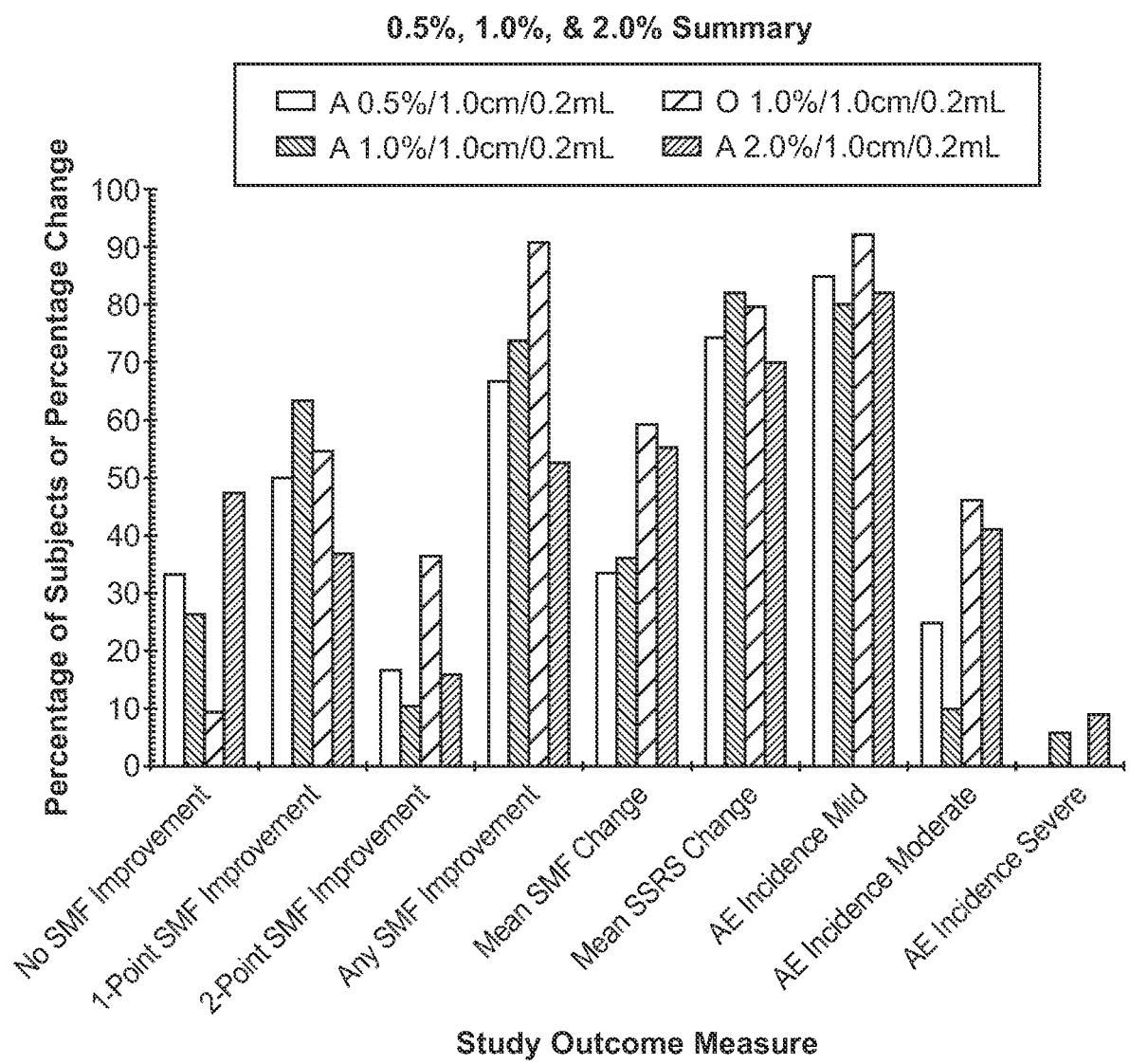
FIG. 24 shows the summary comparison results using different types of visual assessment methods and shows the results of adverse event (AE) observations.

Through repeated numerous analysis, the changes from baseline in SMF rating scale score compared to placebo were found to statistically significant at weeks 8, 12, 16 and 24 for the 0.5% w/v DCA. Statistically significant improvements were seen at weeks 12, 16 and 24 for the 1.0% w/v DCA. Whereas, statistically significant improvements were seen only at week 24 for the 2% w/v DCA all compared against placebo (FIGS. 23 and 24). Therefore, these data show that ATX-101 at 2.0% was less effective than ATX-101 1.0% or 0.5%, as measured by various visual assessment methods.

The data demonstrate that at concentrations at or greater than about 0.5% w/v and less than 2% w/v, unexpectedly superior results are obtained for both efficacy and toxicity (the latter being appropriate only for concentrations at or above 2% w/v) as compared to the results obtained at concentrations above and below this range.

Example 3

This example presents a phase II clinical study demonstrating that, in addition to the appropriate concentrations of sodium deoxycholate, a particular set of clinical treatment protocol showed particular benefit to the patients.

A clinical study was conducted to evaluate the effectiveness of various doses of sodium deoxycholate in removing undesired submental fat (SMF) deposits. This clinical study was multicenter, randomized, double-blind, placebo-controlled study of sodium deoxycholate injection ("SDI" or alternatively "ATX-101") versus placebo for the reduction of localized subcutaneous fat in the submental area (SMF) using magnetic resonance imaging (MRI) and a battery of clinician- and subject-reported measurements.

A total of 274 subjects participated in 6 Phase 1/2 clinical studies that were conducted with SDI. Of these, 3 studies (n=179) evaluated SDI for the treatment of submental fat (SW). Two studies evaluated SDI for the treatment of superficial lipoma. One study (SDI-08-10) evaluated the histological effects of SDI in subcutaneous abdominal tissue in subjects scheduled to undergo abdominoplasty.

SDI was safe and well tolerated at all concentrations in clinical studies. Adverse events from SDI have not been systemic and have generally involved local, transient injection site reactions of mild to moderate intensity. The most commonly observed adverse events associated with the treatment area include pain, erythema, induration, swelling, bruising, and numbness. Less frequently, pruritus and paresthesia have been reported. Across studies, the 0.5% and 1.0% concentrations demonstrated a better safety profile than the higher concentrations (2.0% and 4.0%). The pharmacokinetics of SDI is linear, illustrating the predictable overall exposure. Plasma concentrations were transient with peak concentrations observed at approximately 15 to 30 minutes, returning to endogenous deoxycholate levels within 24 hours after dosing.

The SMF scale used to assess efficacy in clinical studies with SDI has been validated and shown to be reliable. Changes in scores from the Clinician Reported-SW Rating Scale (CR-SMFRS) and Patient Reported-Subject Satisfaction Rating Scale (PR-SSRS) demonstrate that patients respond to therapy. The expected improvement from treatment with SDI is consistent with what patients who desire aesthetic changes would find satisfactory. In clinical studies that evaluated SDI for the treatment of submental fat, changes in SMFRS score at Week 16 and SSRS scores for the doses selected for evaluation in this study (0.5% [0.2 mL/1.0 cm] and 1.0% [0.2 mL/1.0 cm]) were significantly better than placebo. Both treatment regimens also showed a significant change in SMFRS score compared to placebo prior to Week 16.

Study Design

FIG. 2 depicts the study Design and Treatment Schema associated with this procedure. This was a multicenter, randomized, double-blind, placebo-controlled study in which approximately 120 subjects received either up to 50 mg SDI, up to 100 mg SDI, or placebo in a 1:1:1 ratio (5 mg/mL:10 mg/mL:placebo) as indicated below, to evaluate the safety and efficacy of fixed concentrations of SDI given in up to 50 0.2-mL injections in up to 6 treatment sessions. No subject received more than 10 mL in any treatment session, nor did any subject undergo more than 6 treatment sessions. The initial 30 subjects were enrolled in a 2:2:1 ratio (i.e., 12, 12 and 6 subjects per group, for the two SDI groups and placebo, respectively) and the remaining subjects were randomized to balance the enrollment (approximately 28, 28, and 34 per group for the two SDI groups and placebo, respectively). This resulted in a distribution of approximately 40 subjects per treatment group.

All qualified subjects had a baseline MRI completed during the screening period to evaluate pre-treatment SMF volume and thickness. To measure changes in SMF volume and thickness, MRI acquisitions were repeated prior to each treatment session and post-treatment (4 and 12 weeks after the last treatment cycle). Before subjects completed each MRI visit, the MRI images were evaluated for acceptability.

The groups were dosed as in Table 1.

TABLE 1

Dosage

| Treatment | # of Injections | Distance Between Injections | Amount per Injection | # of Subjects |
|---|---|---|---|---|
| Placebo | Up to 50 | Approximately 1.0 cm apart | 0.2 mL | 40 |
| SDI (5 mg/mL) | Up to 50 | Approximately 1.0 cm apart | 0.2 mL | 40 |
| SDI (10 mg/mL) | Up to 50 | Approximately 1.0 cm apart | 0.2 mL | 40 |

Subjects who successfully completed screening and baseline evaluations received up to 50 injections (0.2 mL each for a maximum volume of 10 mL) per treatment session, depending upon size and configuration of the SMF. Treatment was given at 4-week (±5 days) intervals. Study material injection sites were positioned using a 1.0 cm grid, which is designed to achieve an appropriate distribution of injections across the submental area.

Study Material, Dose, and Route of Administration

SDI (sodium deoxycholate injection) was provided in a concentration of 5 mg/mL (0.5%) and 10 mg/mL (1.0%) in 10 mM sodium phosphate, 0.9% (weight per volume [w/v]) sodium chloride, and 0.9% (w/v) benzyl alcohol in water for injection (WFI). Each vial (for single use only) contained at least 2.0 mL of accessible material, accessed by means of sterile syringe and needle through a rubber stopper closure.

Matching placebo consists of the vehicle formulation (10 mM sodium phosphate, 0.9% [w/v] sodium chloride, and 0.9% [w/v] benzyl alcohol in WFI).

Packaging

Study material (SDI 0.5%, SDI 1.0%, and placebo) was provided in subject treatment kits. Each subject treatment kit contained a sufficient number of vials of study material (SDI or placebo) to administer all required doses for the study (i.e., each kit had enough vials for 6 treatment sessions).

Evaluation of Safety

The safety of 5 mg/mL SDI and 10 mg/mL SDI transcutaneous injections in the submental area was evaluated relative to placebo by assessing the spontaneous adverse event reports, clinical evaluation of the submental area, and laboratory test results. The criteria for the safety evaluation included: spontaneously reported adverse events, laboratory test results, treatment area evaluations including scoring of edema, bruising, dysphasia, dysphonia, erythema, hyperpigmentation, hypopigmentation, induration, numbness, pain, paresthesias, and pruritus.

Evaluation of Efficacy

The effects of 5 mg/mL SDI and 10 mg/mL SDI transcutaneous injections in the submental area were evaluated relative to placebo by measuring the following: (1) the reduction of fat using Clinician-Reported Submental Fat Rating Scale (CR-SMFRS), Patient-Reported Submental Fat Rating Scale (PR-SMFRS), and Patient-Reported Submental Fat Impact Scale (PR-SMFIS); (2) the volume of SMF using MRI; and (3) the thickness of SMF using MRI. The efficacy evaluation criteria included: Clinician-Reported Submental Fat Rating Scale (CR-SMFRS), Patient-Reported Submental Fat Rating Scale (PR-SMFRS), Patient-Reported Submental Fat Impact Scale (PR-SMFIS) scores, and Magnetic resonance imaging (MRI).

Other Evaluations

The effects of 5 mg/mL SDI and 10 mg/mL SDI transcutaneous injections in the submental area, relative to placebo, for changes in skin laxity (SLRS), Subject Self Rating Scale (SSRS), and subject-reported outcome measures (Self-Ratings of Attractiveness, Derriford Appearance Scale [DAS], Body Image Quality of Life Inventory [BIQLI]), other Subject-Reported Questions, and Post-treatment Questions) were evaluated. Measurements of the thickness of fat in the submental area were made using calipers. Photographs were taken to document treatment effects. Other criteria for evaluation included: Skin Laxity Rating Scale (SLRS) scores, Subject Self Rating Scale (SSRS) score, Subject-reported outcome measures (Self-Ratings of Attractiveness, Derriford Appearance Scale [DAS], Body Image Quality of Life Inventory [BIQLI]), other Subject-Reported Questions, Subject Global Questions and Post-treatment Questions.

Treatment Procedures

During the screening period, subjects completed all eligibility requirements and otherwise qualify for enrollment, before the baseline MRI is acquired. The baseline MRI was completed before the first treatment was administered at the baseline visit (Week 0). Subjects who successfully completed screening and baseline evaluations received up to 50 injections (0.2 mL each for a maximum volume of 10 mL) per treatment session, depending on size and configuration of the SMF. Treatment was given during up to 6 treatment sessions at 4-week (±5 days) intervals. Injection sites were positioned on a 1.0-cm grid.

Administration of Study Material: Eligible subjects were randomized to 1 of 3 treatment groups in the order in which they completed baseline evaluations:
  Placebo (vehicle): 0.2 mL/injection, up to 50 injections per treatment session
  SDI 5 mg/mL: 0.2 mL/injection, up to 50 injections per treatment session
  SDI 10 mg/mL: 0.2 mL/injection, up to 50 injections per treatment session Dose preparation by authorized site personnel and administration by the investigator is performed according to instructions.

A 30-gauge, 0.5-inch needle attached to a 1-mL syringe was used to administer study material. Injections were given transcutaneously directly into the fat tissue.

Injection sites were positioned to achieve an appropriate distribution of study material injections across the target location. The following procedures or instruction of use were provided for use with the administration of study material:

Topical anesthesia (i.e., topical lidocaine preparations, ice) may be applied in the area of the planned injection sites and recorded in the case report form (CRF).
  Up to 50 injections spaced approximately 1.0 cm apart is given. A grid is applied to the treatment area to guide the placement of injections. For each treatment session, injections are given on a 1.0-cm grid pattern across the submental area to be treated. The grid can be applied to the chin of the patient using a tattoo as illustrated in FIG. 25.
  For each study material injection, the investigator palpates the treatment area to determine the approximate thickness of the targeted SMF and inject study material into fat tissue at a depth of approximately mid-way into the SMF.
  If at any time resistance is met as the needle is inserted, indicating the possibility of contact with fascial or nonfat tissue, the needle will be withdrawn to an appropriate depth before the injection is given.
  Upon needle withdrawal, pressure is applied to each injection site for several seconds to minimize bleeding; an adhesive dressing may be applied. Upon completion of the injections, the area may be gently massaged to facilitate distribution of study material.
  At each treatment session, the investigator will determine the number and locations of injections. He or she will evaluate each planned injection location to avoid sites for which an injection may not be appropriate (e.g., nodule formation, significant residual inflammation, or lack of SMF). If a sufficient number of locations are not suitable for injection, the treatment session may be delayed for up to 28 days.
  Subjects may be discharged from the research facility approximately 60 minutes after study material is administered, provided it is medically appropriate to do so.
  Concomitant therapy: Throughout the study, investigators may prescribe any concomitant medications or treatments deemed necessary, with the exception of investigational drugs.

Submental Fat Assessments

Submental fat ratings using the SMFRS were conducted at screening, baseline, and Visits 3, 4, 5, 6, 7, 8, and 9.

The SMFRS score is based on the investigator's clinical evaluation of the subject, including palpation of the chin and neck area; anterior, oblique, and profile views of the chin and neck; and observation of pronation, supination, and lateral movement of the head. The score was determined using the rating scale definitions and the representative photographs associated with each score. The final score was determined while the subject's head is in the Frankfort plane posture as described in the SMFRS. The score was recorded as a whole number. At screening and baseline, the score was determined in conjunction with protocol entry criteria (e.g., absence of loose skin, diffuse SMF, and prominent platysmal bands at rest that interfere with evaluation of localized fat).

Standardized photographs were taken before treatment (baseline and Visits 3, 4, 5, 6, and 7), and post-treatment (Visits 8 and 9) to document treatment effects.

At Visit 9 measurements of the thickness of fat in the submental area were made using calipers.

Clinician reported scores (Table 2) utilized a score card (illustrated in FIG. 3) that shows representative photographs with annotated scores. In this context, the acronym "CR-SMFRS" (clinician-reported submental fat rating scale) is used interchangeably with "SMFRS" (submental fat rating scale).

TABLE 2

Clinician-Reported Submental Fat Rating Scale (CR-SMFRS)

| Score | SMF Description |
|---|---|
| 0 | Absent Submental Convexity: No localized submental fat evident. |
| 1 | Mild Submental Convexity: Minimal, localized submental fat. |
| 2 | Moderate Submental Convexity: Prominent, localized submental fat. |
| 3 | Severe Submental Convexity: Marked, localized submental fat. |
| 4 | Extreme Submental Convexity. |

A separate score, Skin Laxity Rating Scale (SLRS), was based on skin laxity assessment using on clinical evaluation and palpation of the submental area (Table 3).

TABLE 3

Skin Laxity Rating Scale (SLRS)

| Score | Skin Laxity Rating |
|---|---|
| 1 | No Laxity |
| 2 | Minimal Laxity |
| 3 | Moderate Laxity |
| 4 | Very Lax |

Statistical Considerations

The sample size of approximately 40 subjects per SDI treatment group (5 mg/mL, 10 mg/mL) and approximately 40 subjects (placebo) was determined based on clinical rather than statistical considerations.

Results

Figure 4:
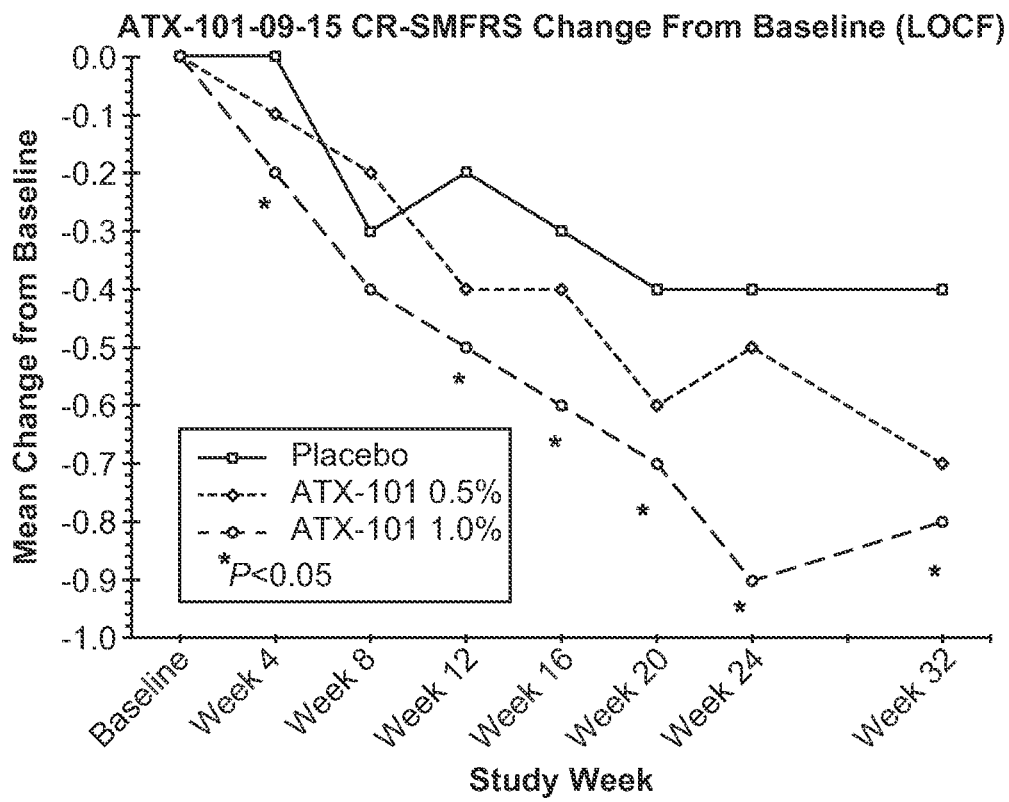
FIG. 4 shows CR-SMFRS changes from baseline for patients receiving the treatment of placebo, 0.5% ATX-101 (0.5% sodium deoxycholate) or 1.0% ATX-101 (1.0% sodium deoxycholate).
Figure 5:
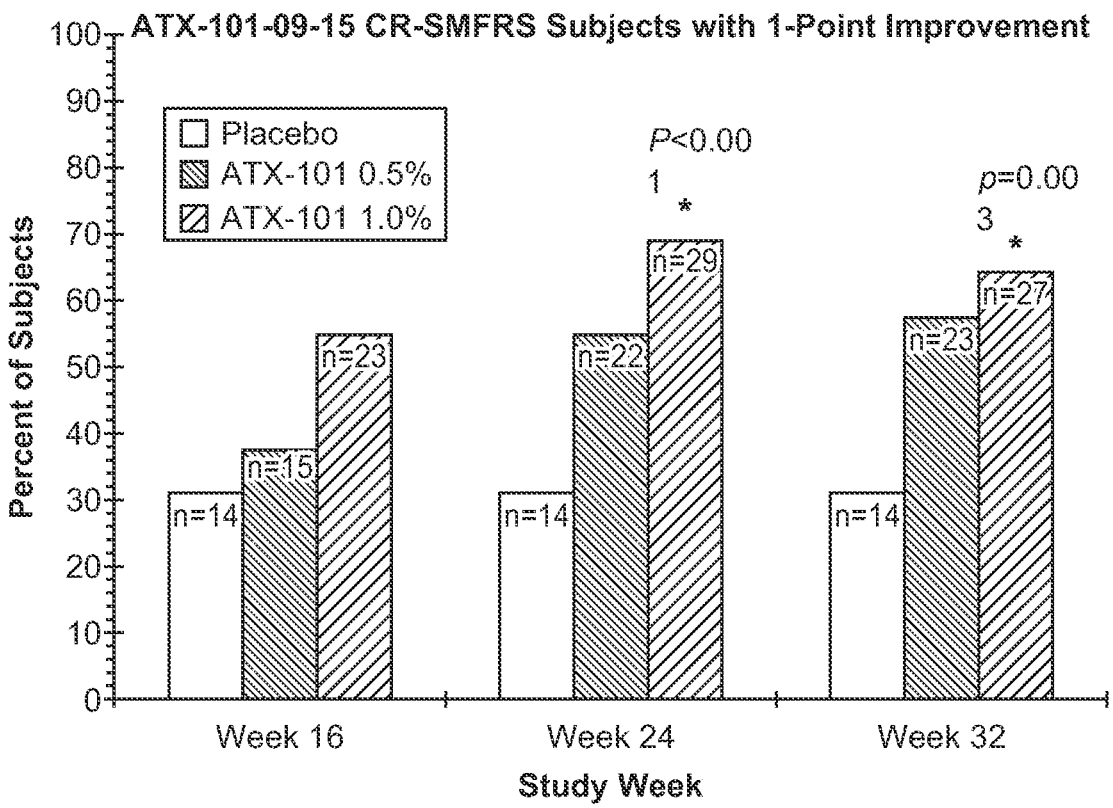
FIG. 5 is a chart showing percentages of subjects with 1-point improvement, as measured by CR-SMFRS, for patients receiving the treatment of placebo, 0.5% ATX-101 or 1.0% ATX-101.

As shown in FIG. 4, both ATX-101 1.0% and 0.5% achieved marked reduction of submental fat as compared with placebo, in which the reduction by ATX-101 1.0% was statistically significant at most time points. Further, at week 16, 24 and 32, the numbers of patients having at least 1-point improvement were greater in the ATX-101 1.0% and 0.5% groups than in the placebo group (FIG. 5).

Figure 6:
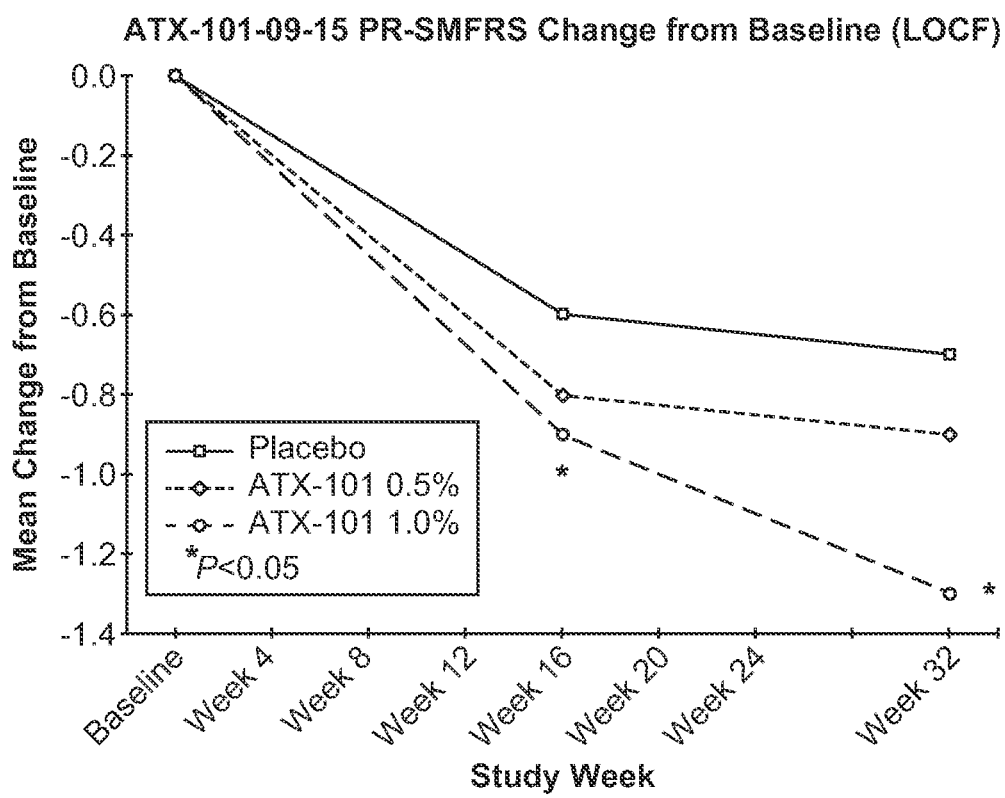
FIG. 6 shows PR-SMFRS changes from baselines for patients receiving the treatment of placebo, 0.5% ATX-101 or 1.0% ATX-101.
Figure 7:
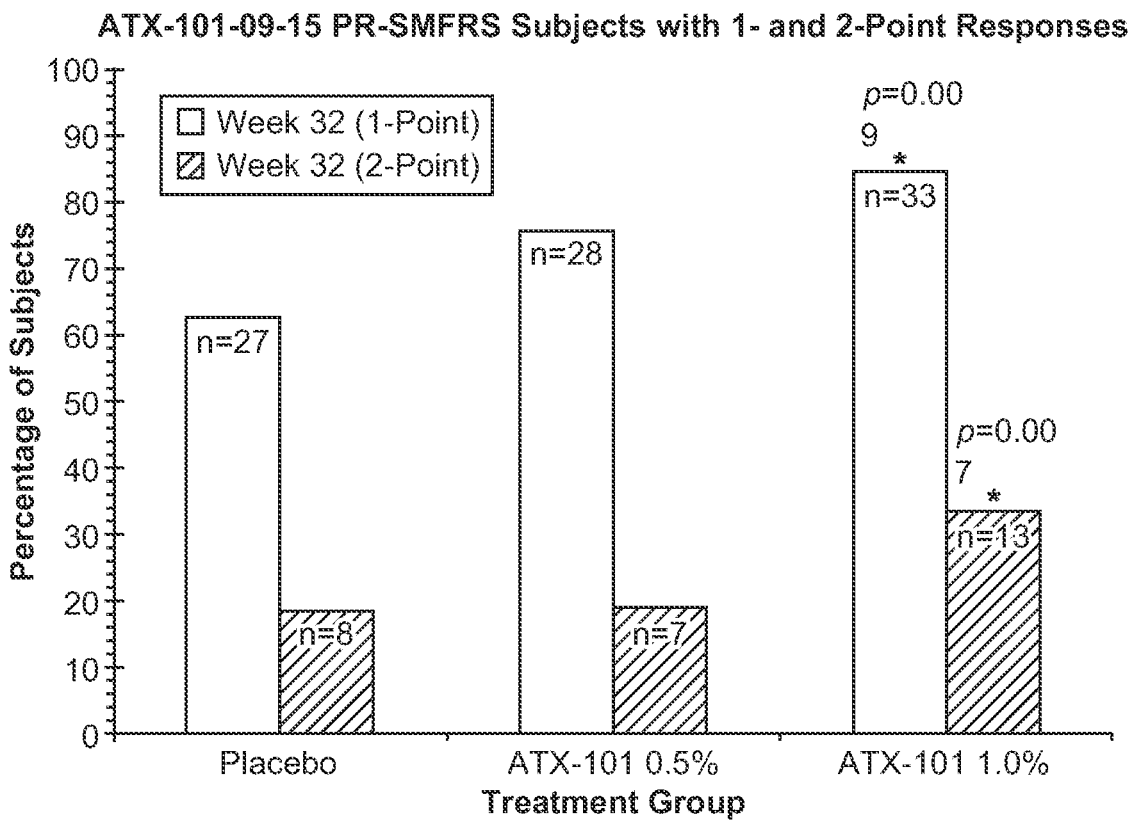
FIG. 7 shows percentages of subjects with 1- and 2-point improvement, as measured by PR-SMFRS, for patients receiving the treatment of placebo, 0.5% ATX-101 or 1.0% ATX-101.
Figure 8:
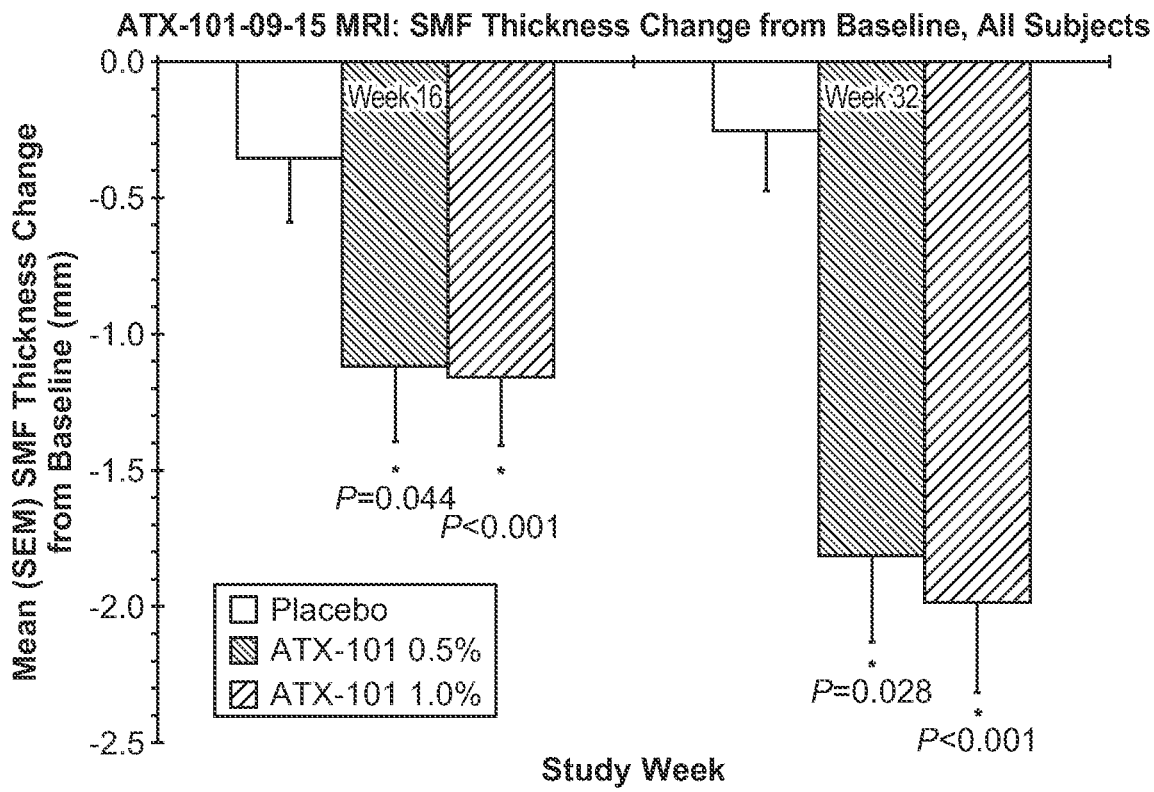
FIG. 8 shows SMF changes, as measured by MRI, from baseline for patients receiving the treatment of placebo, 0.5% ATX-101 or 1.0% ATX-101.
Figure 9:
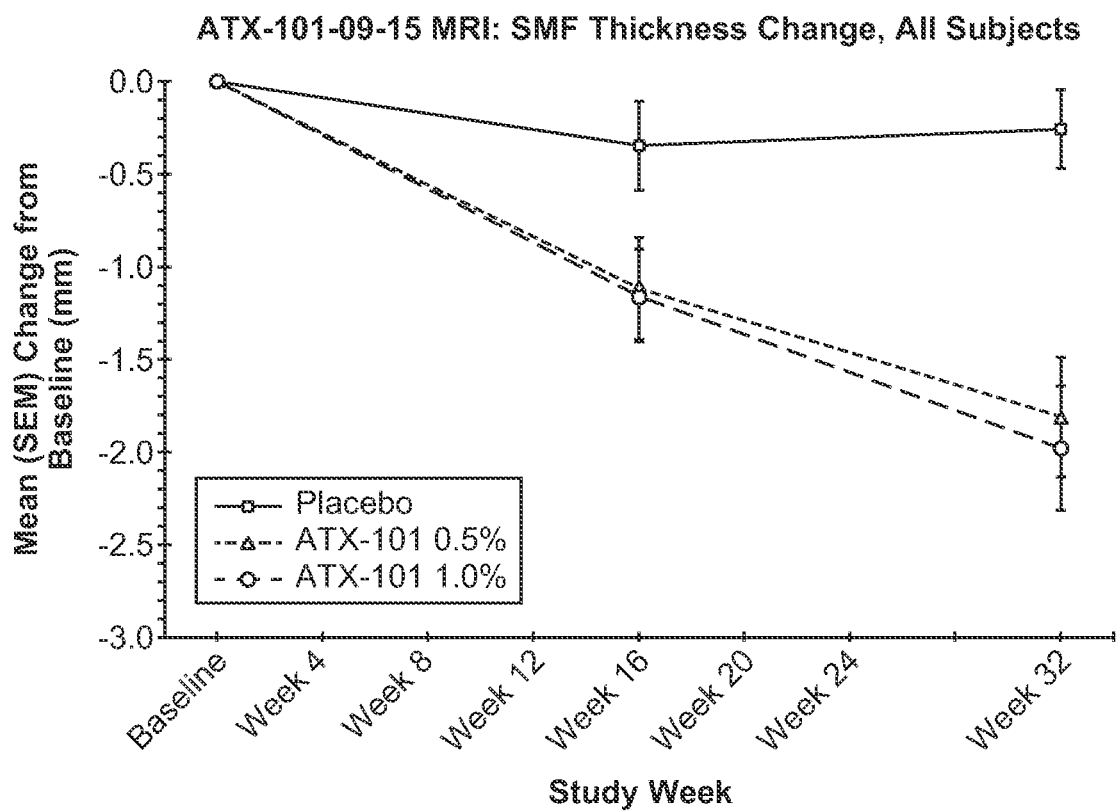
FIG. 9 shows SMF thickness changes for all subjects at week 16 and 32.
Figure 10:
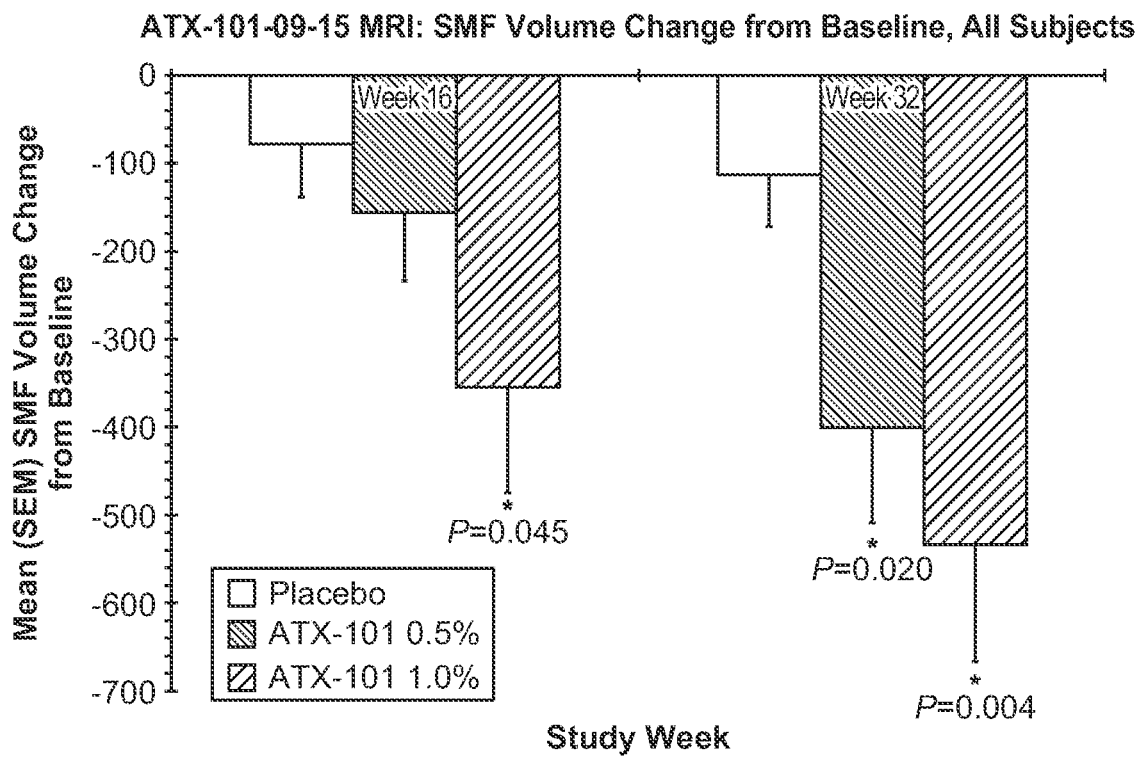
FIG. 10 shows SMF volume changes from baseline, as measured by MRI.
Figure 11:
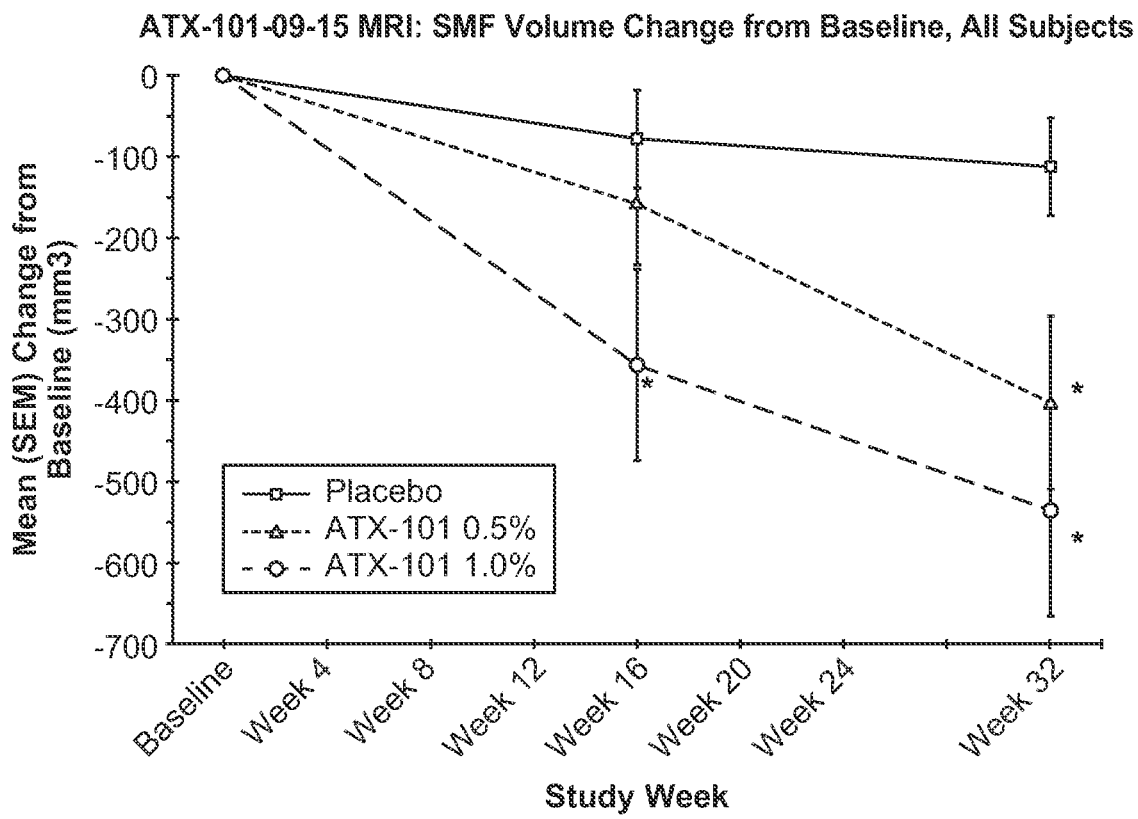
FIG. 11 shows SMF volume changes from baseline, as measured by MRI, as curves.
Figure 12:
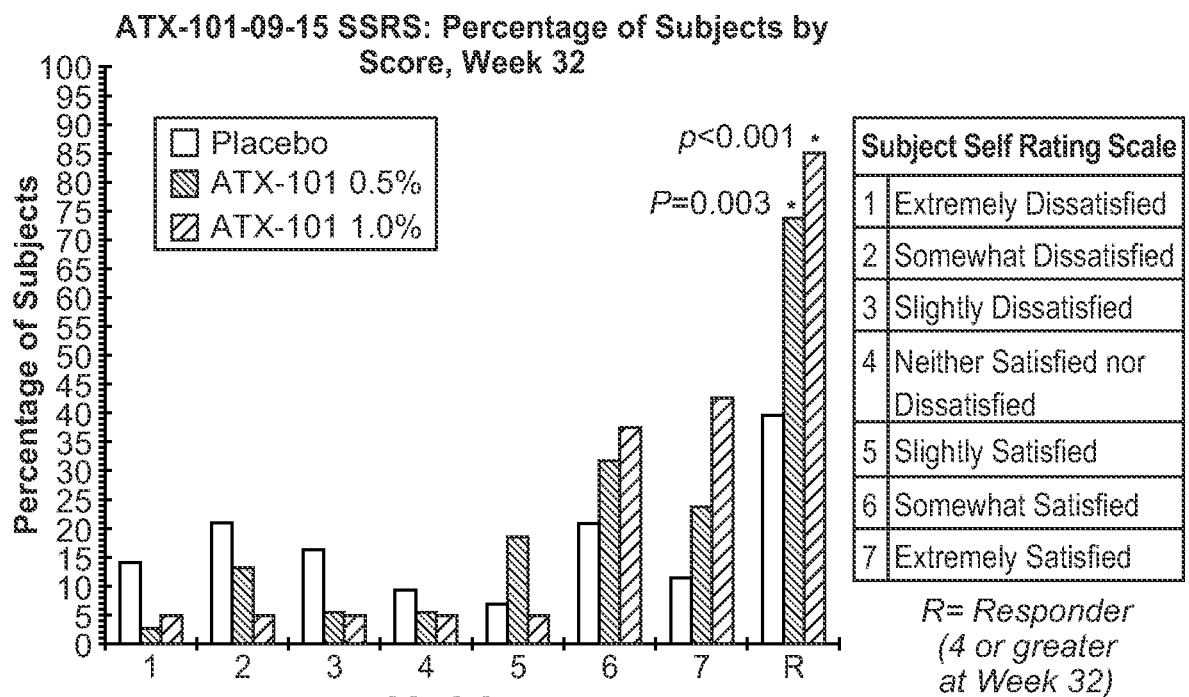
FIG. 12 is chart revealing the results based on subject self rating scales.
Figure 13:
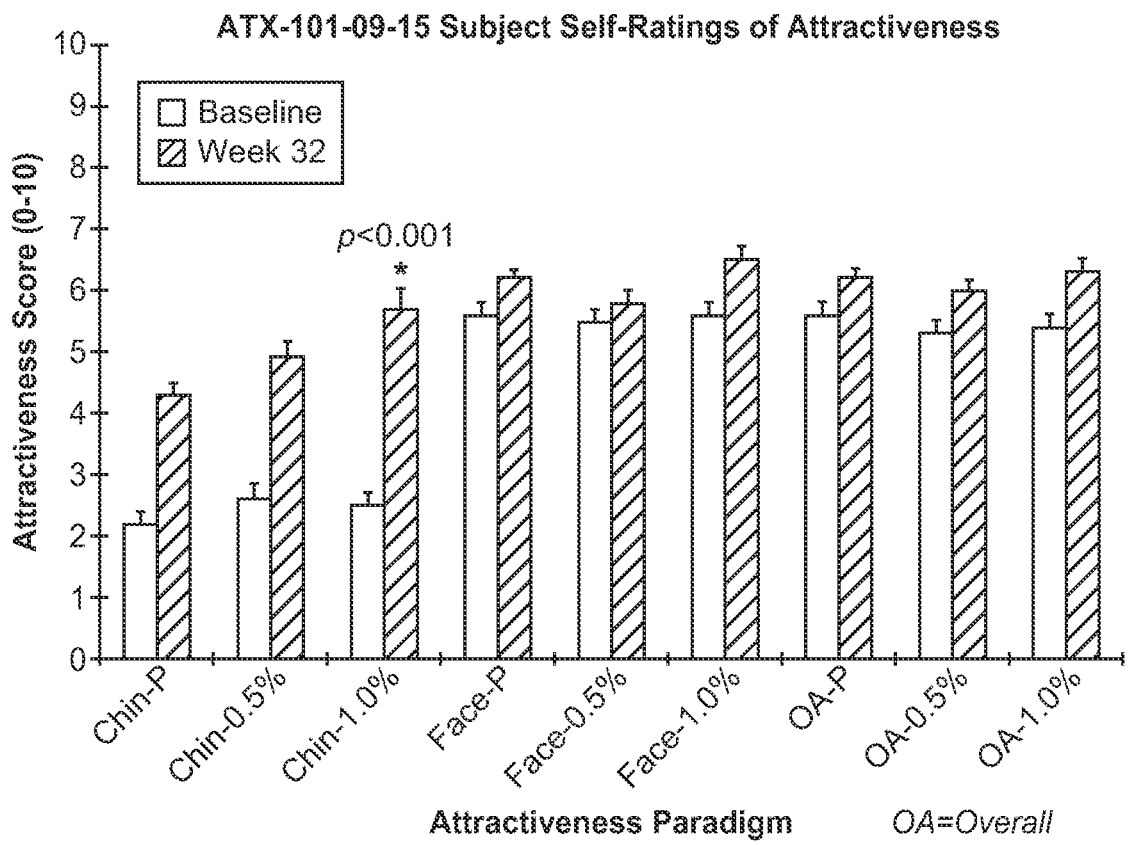
FIG. 13 presents data from subject self-rating of attractiveness.

Similar results were reported by the self-assessment of the patients (FIGS. 6 and 7) and by measurement of MRI (FIG. 8-11). Likewise, assessments based on Patient Reported-Subject Satisfaction Rating Scale (SSRS) (FIG. 12) and subject self-rating of attractiveness (FIG. 13) confirmed the success of the treatments using ATX-101 1.0% and 0.5%.

One of the self assessments was Patient Reported Submental Fat Impact Scale (PRSMFIS). An illustrative questionnaire is shown as follows (all questions follow a 0-10 point scale):

1. How happy are you with the appearance of your chin fat?
2. How bothered are you by the appearance of your chin fat?
3. How self-conscious are you about the appearance of your chin fat?
4. How embarrassed are you about the appearance of your chin fat?
5. How much older do you look because of your chin fat?
6. How much overweight do you look because of your chin fat?

A statistically significant different ($p<0.01$) was achieved for the ATX-101 1.0% on all measures at week 32.

Still another assessment, based on the following questionnaire, showed a statistically significant different ($p<0.01$) for both ATX-101 1.0% and 0.5% on all measures at week 32:

1. Since the start of the study, how would you rate the fat under your chin right now?
2. Since the start of the study, how would you rate the definition between your chin and neck right now?
3. How satisfied are you with the treatment you received in this study?

Each question followed a 7-point scale: a great deal worse, moderately worse, a little worse, about the same, moderately better, and a great deal better.

Figure 14:
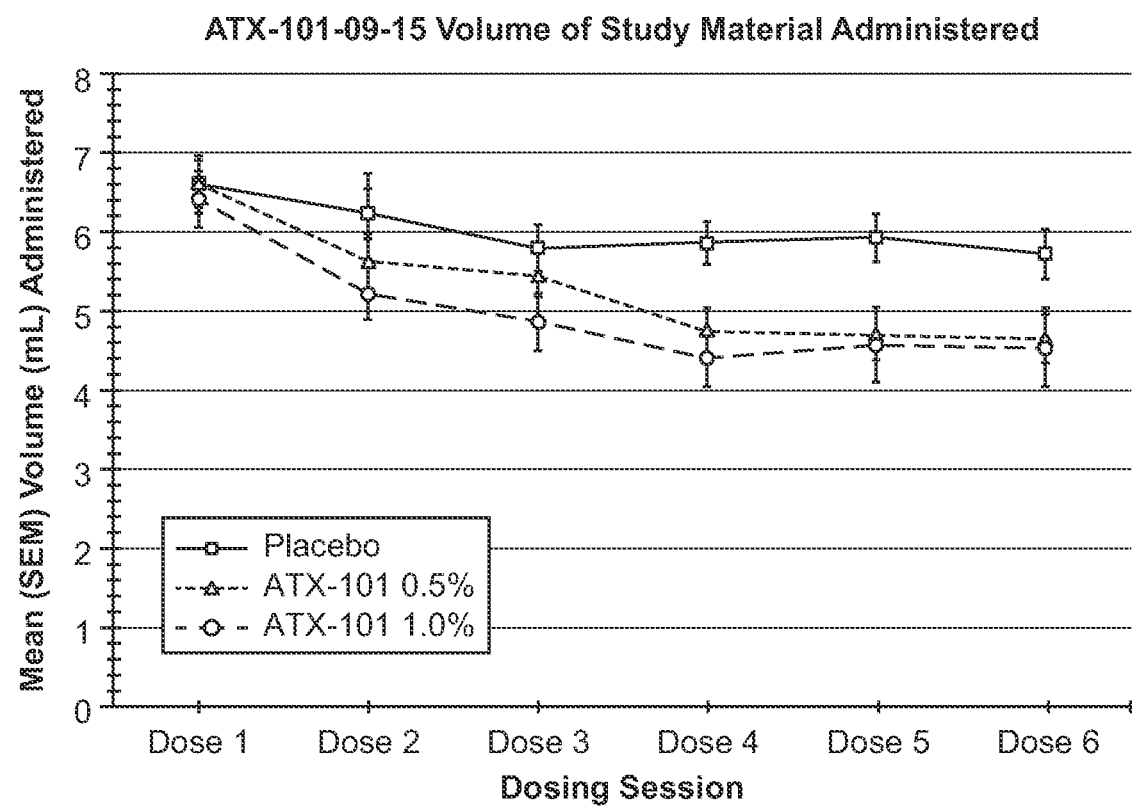
FIG. 14 shows the volume of study materials used in each treatment group, at different time points.
Figure 15:
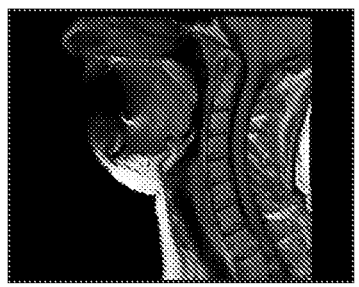
FIG. 15 presents MRI images of a representative patient before and after the treatment with 0.5% ATX-101.
Figure 15:
Figure 16:
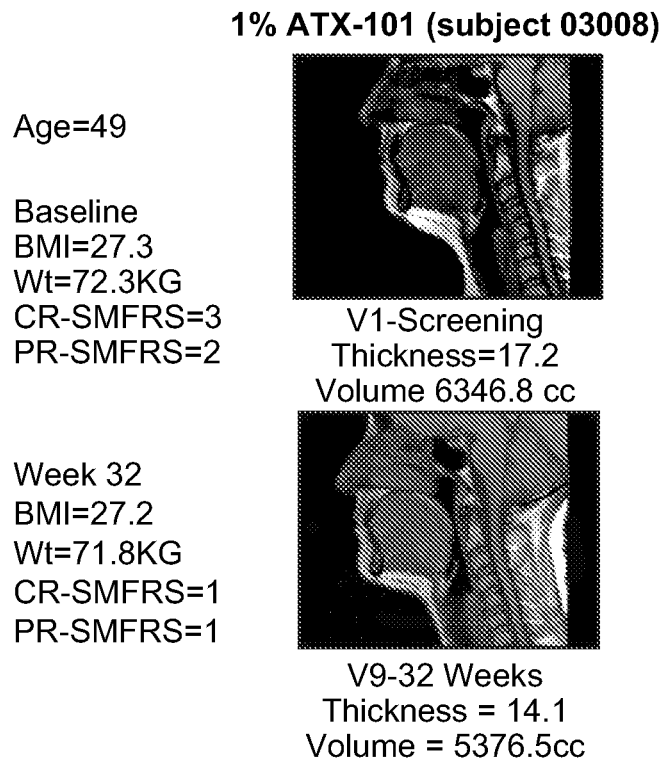
FIG. 16 presents MRI images of a representative patient before and after the treatment with 1.0% ATX-101.

FIGS. 15 and 16 include representative MRI images, before and after the treatment, for ATX-101 0.5% and 1.0%, respectively. FIG. 14 shows the volume of study materials used in each treatment group, at different time points.

Figure 17:
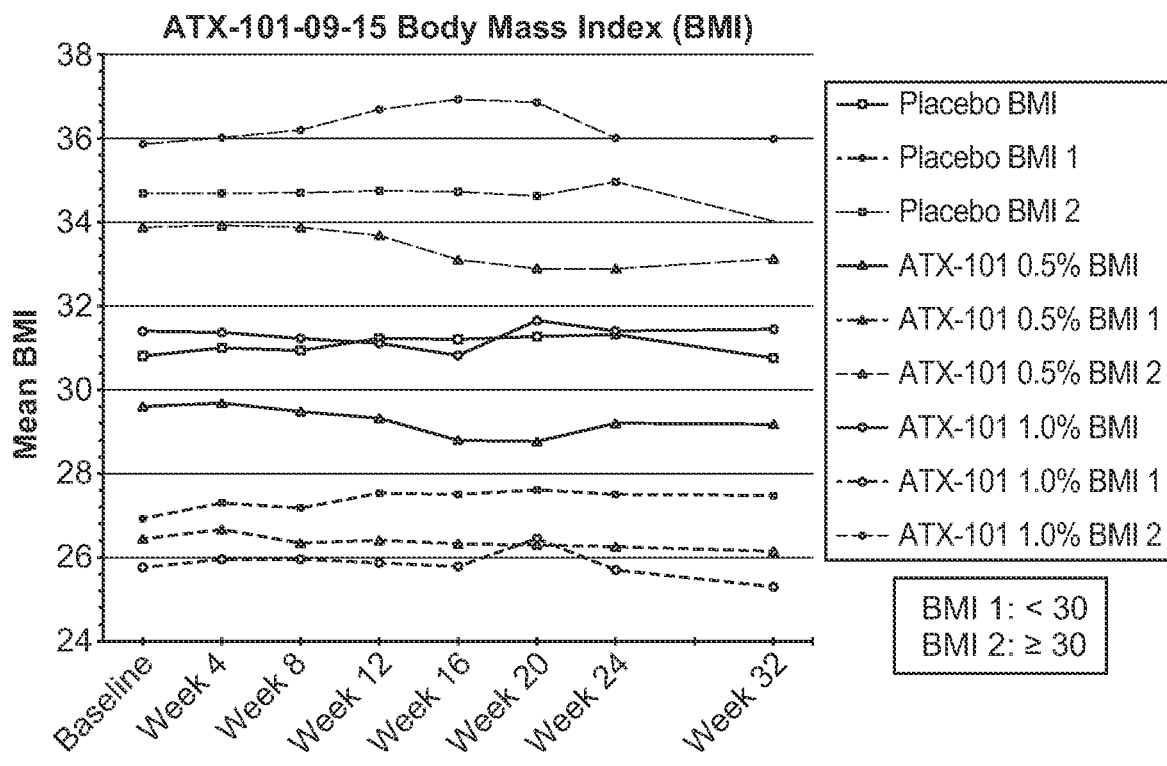
FIG. 17 shows the body mass index (BMI) of subjects undergoing the treatments.
Figure 18:
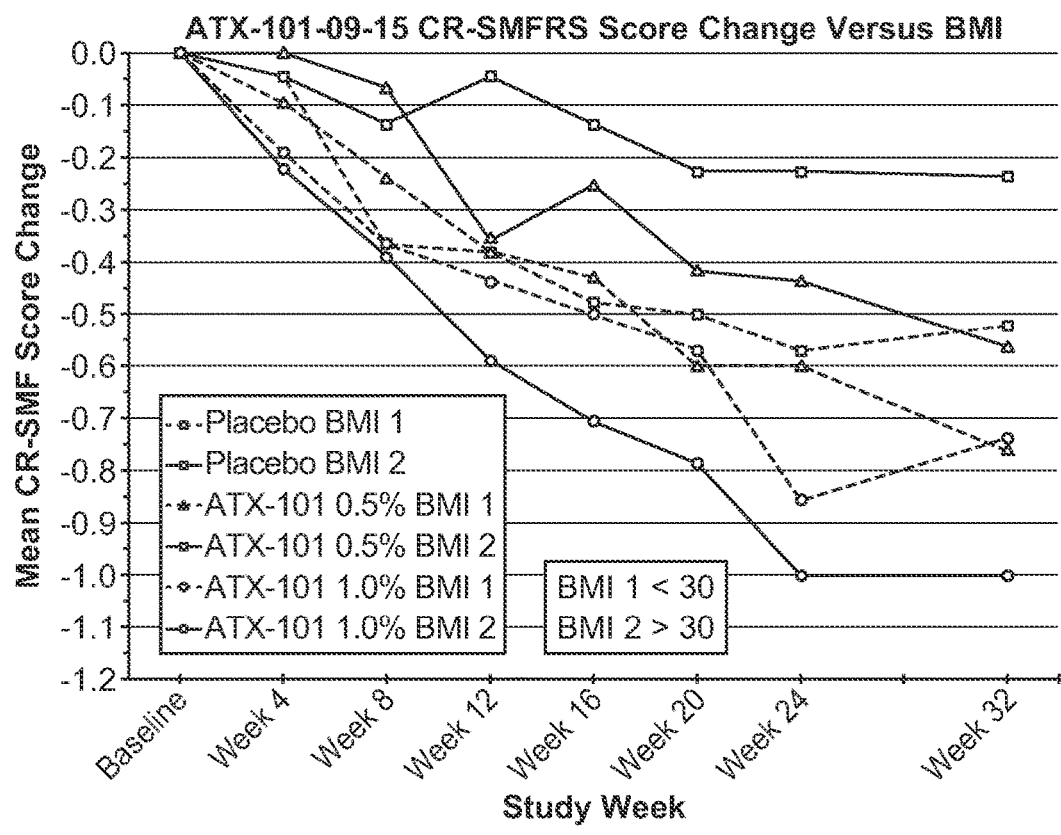
FIG. 18 shows the CR-SMFRS score/BMI ratios for the subjects in each treatment group.

FIG. 17 shows that patients receiving the treatments did not have marked changes of their body mass index (BMI). Nevertheless, using the BMI as a standard, ATX-101 treatments resulted in significant submental fat reduction, as measured by CR-SMFRS (FIG. 18).

Figure 19:
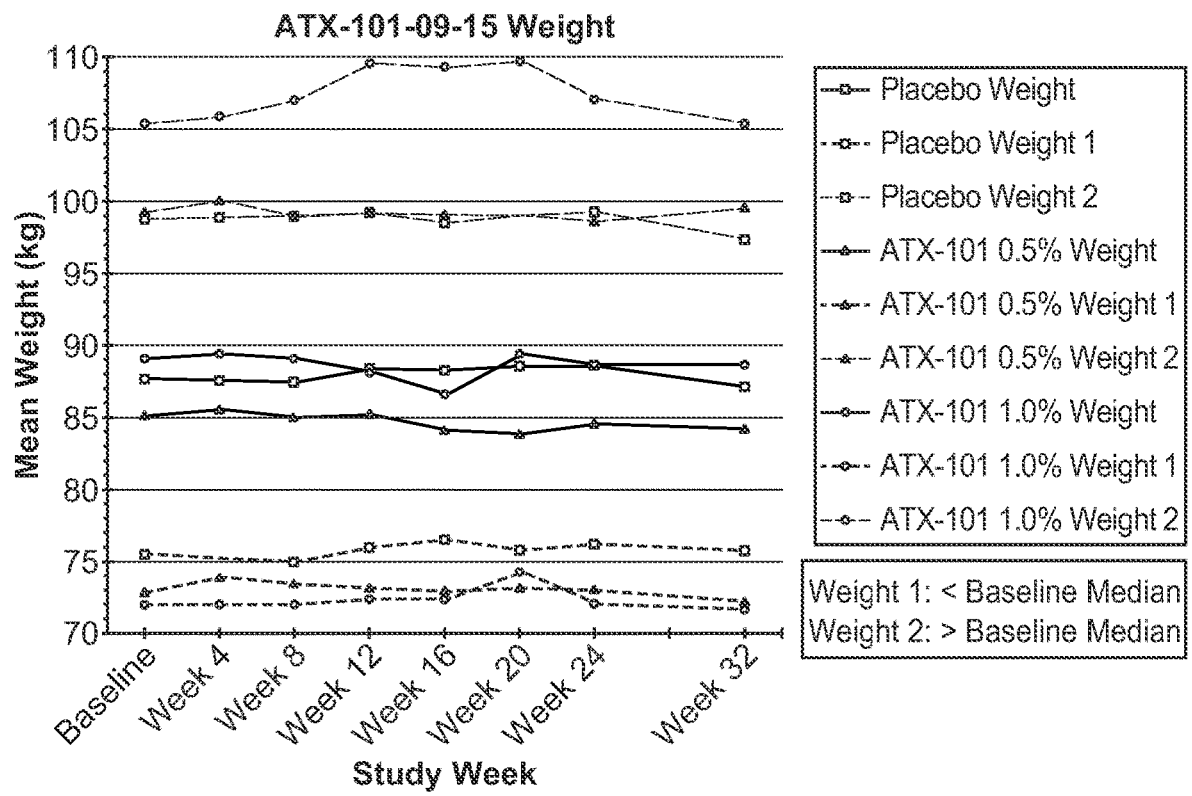
FIG. 19 shows the body weight of subjects undergoing the treatments.
Figure 20:
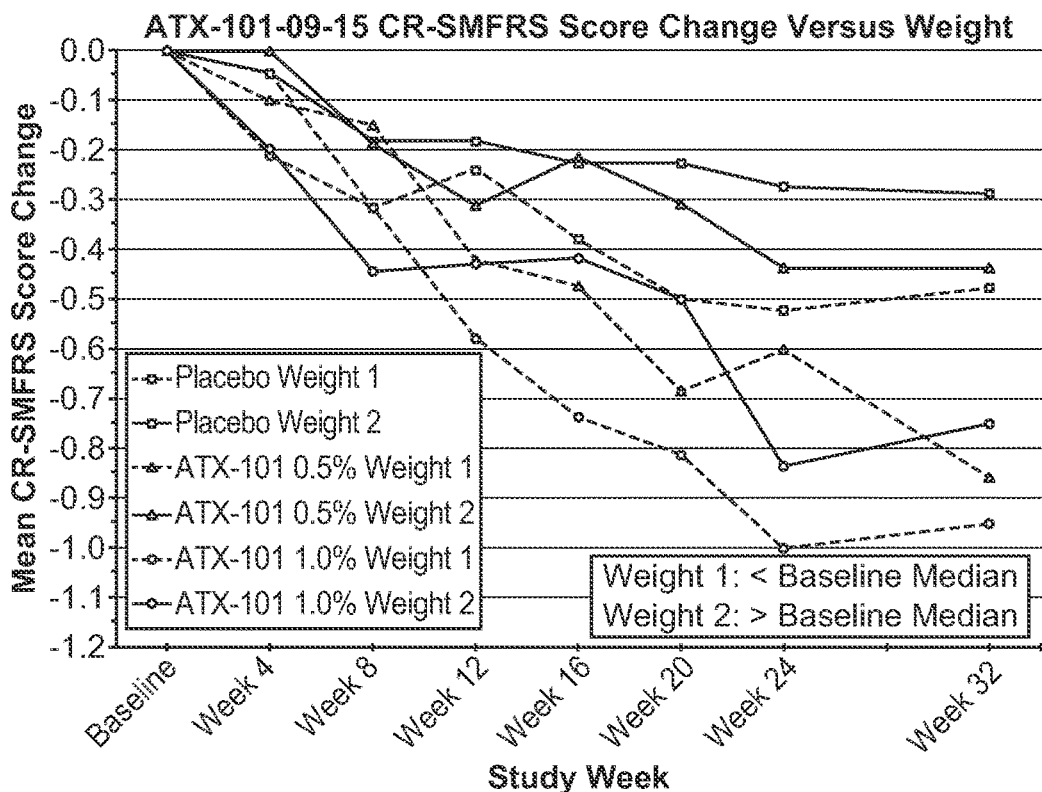
FIG. 20 shows the CR-SMFRS score/body weight ratios for the subjects in each treatment group.
Figure 21:
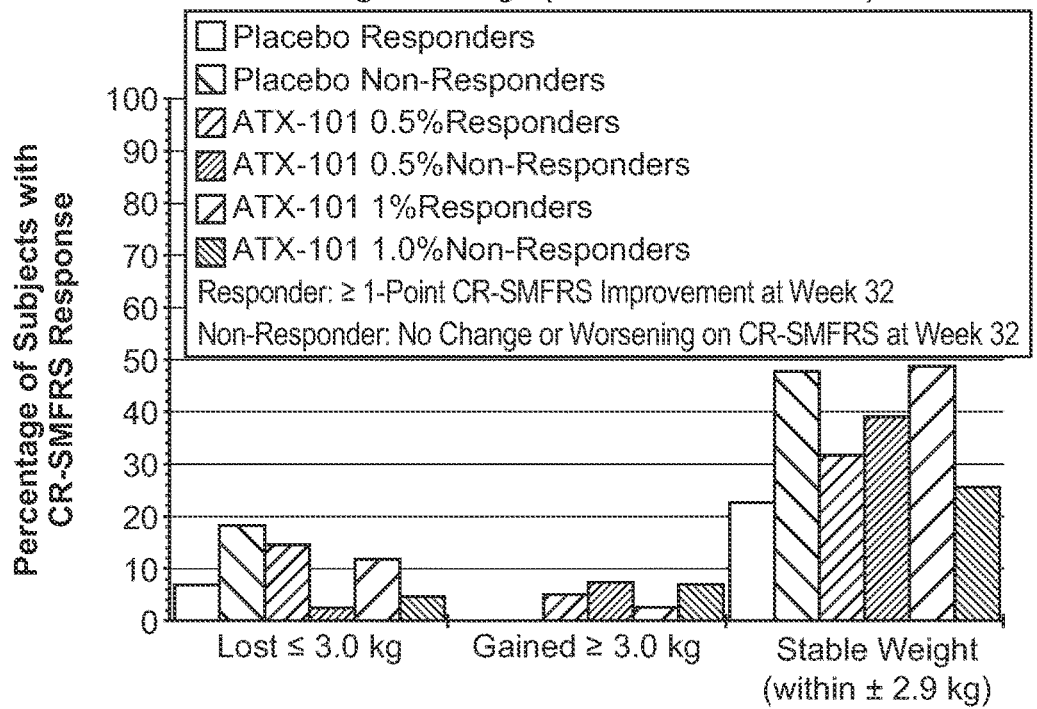
FIG. 21 shows the percent of CR-SMFRS responders by weight change, at week 32.

Likewise, the body weight of the patients did not undergo obvious changes during the course of the treatments (FIG. 19), but the CR-SMFRS/body weight ratio decreased significantly (FIGS. 20 and 21).

Figure 22:
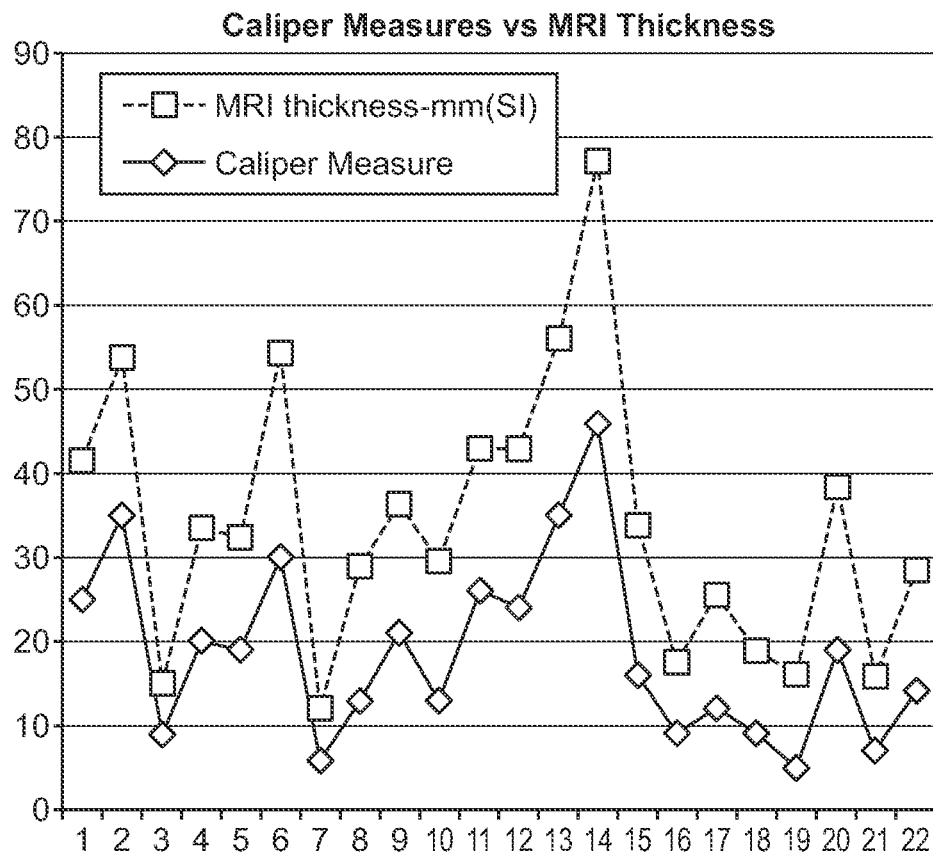
FIG. 22 shows the correlation between caliper measurement and MRI thickness measurement.

In terms of quality of treatment outcome assessment, FIG. 22 shows a good correlation between caliper measurement and MRI evaluation.

In summary, as measured by CR-SMRFS, both ATX-101 1.0% and 0.5% showed good dose response, yet the 1.0% dose was more effective than 0.5%. Statistically significance was obtained for 1-grade reduction for the 1.0% dose at week 16 and week 32.

Using PR-SMFRS, both ATX-101 1.0% and 0.5% also showed good dose response, and the 1.0% dose was more effective than 0.5%. Statistically significance was obtained for 1-grade reduction for the 1.0% dose at week 16 and week 32, and 2-grade reduction for the 1.0% dose at week 32.

Determined by MRI, statistically significant reduction of both MRI and thickness and volume was observed with both 0.5% and 1.0% doses, whereas 1.0% showed better dose response and greater reduction.

Still in other measurements, statistically significant changes, along with dose response, were observed for both doses, in SSRS, in patient impact scores, in patient impact questionnaire, and in improvement in appearance of the chin and satisfaction.

This example, therefore, shows the clinical efficacy of ATX-101, at both 0.5% and 1.0% doses, as well as the benefit of the clinical procedure. Moreover, this example further validates the utility of various assessment methods employed here, including the score card used by clinicians.

The embodiments and example described above are not intended to limit the disclosure. It should be understood that numerous modifications and variations are possible in accordance with the principles of the present disclosure.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A method for decreasing submental fat in a subject, said method comprising
   (a) applying a grid pattern to mark injection sites spaced about 1.0 cm apart from each other at a treatment area of the subject; and
   (b) administering a plurality of subcutaneous injections to the treatment area, one injection administered per injection site as marked by the grid pattern;
   wherein each injection comprises a solution comprising about 2 mg of deoxycholic acid, or a salt thereof, the solution is free of phosphatidylcholine; each injection has a volume of about 0.2 mL; the plurality of subcutaneous injections contains up to 24 injections; and steps (a) and (b) are repeated up to 3 times at 4-week intervals.

2. The method of claim 1, further comprising massaging the treatment area after completion of the administration of the plurality of subcutaneous injections.

3. The method of claim 1, wherein the plurality of subcutaneous injections has a total volume of up to 10 mL.

4. The method of claim 1, wherein each injection is administered using a syringe with a 30-gauge, 0.5-inch needle.

5. The method of claim 1, further comprising administering to the subject an agent selected from the group consisting of anesthetic agents, anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, anti-diarrhea agents, and any combinations thereof.

6. The method of claim 1, further comprising administering lidocaine to the treatment area prior to the administering of the plurality of subcutaneous injections.

7. The method of claim 1, wherein each injection further comprises a lipase.

8. The method of claim 1, wherein the solution further comprises benzyl alcohol at a concentration of about 0.8% w/w to about 1% w/w.

9. A method for decreasing submental fat in a subject, said method comprising
   (a) applying a grid pattern to mark injection sites spaced about 1.0 cm apart from each other at a treatment area of the subject;
   (b) palpating the treatment area prior to administering the plurality of subcutaneous injections; and
   (c) administering a plurality of subcutaneous injections to the treatment area, one injection administered per injection site as marked by the grid pattern;
   wherein each injection comprises a solution consisting essentially of 2 mg of deoxycholic acid, or a salt thereof; each injection has a volume of 0.2 mL; each injection is administered at a depth of approximately mid-way into the submental fat; the plurality of subcutaneous injections contains up to 24 injections; and steps (a) and (b) are repeated up to 3 times at 4-week intervals.

10. The method of claim 9, further comprising massaging the treatment area after completion of the administration of the plurality of subcutaneous injections.

* * * * *